United States Patent
Gray et al.

(10) Patent No.: US 7,131,967 B2
(45) Date of Patent: *Nov. 7, 2006

(54) INFUSION DEVICE AND DRIVING MECHANISM FOR SAME

(75) Inventors: John F. Gray, Woodland Hills, CA (US); Robert W. Bosley, Cerritos, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/369,242

(22) Filed: Feb. 19, 2003

(65) Prior Publication Data

US 2003/0135160 A1   Jul. 17, 2003

Related U.S. Application Data

(62) Division of application No. 10/033,722, filed on Dec. 27, 2001.

(60) Provisional application No. 60/317,886, filed on Sep. 7, 2001.

(51) Int. Cl.
*A61K 9/22* (2006.01)

(52) U.S. Cl. ............... 604/891.1; 604/131; 604/152

(58) Field of Classification Search ........... 604/890.1, 604/811.1, 131, 93.01, 151, 152; 417/415–417, 417/44.1, 45, 44.11; 128/DIG. 12
See application file for complete search history.

(56) References Cited

U.S. PATENT DOCUMENTS

| | | | |
|---|---|---|---|
| 4,021,152 A | 5/1977 | Toyoda | |
| 4,193,397 A | 3/1980 | Tucker et al. | |
| 4,245,789 A * | 1/1981 | Gray | 239/585.2 |
| 4,373,527 A | 2/1983 | Fischell | |
| 4,373,527 A | 2/1983 | Fischell | |
| 4,391,620 A | 7/1983 | Geisel | |
| 4,437,815 A | 3/1984 | McMullen | |
| 4,468,221 A | 8/1984 | Mayfield | |
| 4,557,726 A | 12/1985 | Reinicke | |
| 4,568,250 A | 2/1986 | Falk et al. | |
| 4,569,641 A | 2/1986 | Falk et al. | |
| 4,573,994 A | 3/1986 | Fischell et al. | |
| 4,576,556 A | 3/1986 | Thompson | |
| 4,594,058 A | 6/1986 | Fischell | |
| 4,636,150 A | 1/1987 | Falk et al. | |
| 4,684,368 A | 8/1987 | Kenyon | |
| 4,692,147 A | 9/1987 | Duggan | |
| 4,697,622 A | 10/1987 | Swift et al. | |
| 4,714,234 A | 12/1987 | Falk et al. | |
| 4,808,089 A | 2/1989 | Buchholtz et al. | |
| 4,883,467 A | 11/1989 | Franetzki et al. | |

(Continued)

*Primary Examiner*—Kevin C. Sirmons
*Assistant Examiner*—Benjamin Huh
(74) *Attorney, Agent, or Firm*—Foley & Lardner LLP

(57) ABSTRACT

A drive mechanism for delivery of infusion medium. A coil surrounds a piston channel. An armature is located adjacent the coil. The armature is moveable toward a forward position in response to the electromagnetic field produced by activation of the coil. A piston located within the piston channel is moveable within the channel to a forward position in response to movement of the armature. The armature and piston are moved toward a retracted position when the coil is not energized. In the retracted position, a piston chamber formed between the piston and a valve member is filled with infusion medium. As the piston is moved to its forward position, piston chamber volume is reduced and pressure within the piston chamber increases and moves the valve member into an open position. Medium from the piston chamber is then discharged into an outlet chamber.

36 Claims, 23 Drawing Sheets

U.S. PATENT DOCUMENTS

| | | |
|---|---|---|
| 4,985,015 A | 1/1991 | Obermann et al. |
| 5,167,633 A | 12/1992 | Mann et al. |
| 5,176,644 A | 1/1993 | Srisathapat et al. |
| 5,318,521 A | 6/1994 | Slettenmark |
| 5,492,449 A | 2/1996 | Hunklinger et al. |
| 5,514,103 A | 5/1996 | Srisathapat et al. |
| 5,527,307 A | 6/1996 | Srisathapat et al. |
| 5,797,733 A | 8/1998 | Falk et al. |
| 5,975,437 A * | 11/1999 | Streicher et al. ......... 239/585.3 |
| 6,142,445 A | 11/2000 | Kawaguchi et al. |
| 6,193,477 B1 | 2/2001 | Falk et al. |
| 6,227,818 B1 | 5/2001 | Falk et al. |
| 6,652,252 B1 | 11/2003 | Zabar |
| 6,932,584 B1 * | 8/2005 | Gray et al. ................. 417/417 |

* cited by examiner

INFUSION DEVICE AND DRIVING MECHANISM FOR SAME

This is a Divisional Application of application Ser. No. 10/033,722, filed Dec. 27, 2001, which is in turn a non-provisional of application Ser. No. 60/317,886 filed Sep. 7, 2001.

CROSS-REFERENCE TO RELATED APPLICATIONS

Embodiments of the present invention claim priority from a U.S. Provisional Application entitled "Infusion Device and Driving Mechanism For Same," Ser. No. 60/317,886, filed Sep. 7, 2001, the contents of which are incorporated by reference herein.

FIELD OF THE INVENTION

The present invention relates generally to infusion devices, systems and processes and, in particular embodiments to implantable infusion devices, systems and processes employing a drive mechanism configuration which allows the device to have a relatively thin form factor and use power efficiently. Further embodiments of the invention relate to drive mechanisms and processes of making and using such drive mechanisms for infusion devices and systems.

RELATED ART

Infusion devices are typically used to deliver an infusion media, such as a medication, to a patient. Implantable infusion devices are designed to be implanted in a patient's body, to administer an infusion media to the patient at a regulated dosage. Because implantable infusion devices are designed to be implanted in the patient's body, the dimensions of such devices can have an impact on the determination of the location in the body at which a device may be implanted, the level of comfort of the implant patient and the external appearance of the implant site. Typically, a device with relatively small dimensions and, in particular, a relatively small thickness form factor, will provide greater flexibility in the choice of location in the patient's body to place the implant and will minimize patient discomfort and minimize noticeable protrusions at the implant site. Accordingly, there is a demand in the industry for minimizing the overall dimensions, and, in particular, the thickness dimension of implantable infusion device.

In some contexts of use, the infusion device must be operable for an extended period with a limited power supply. For example, battery powered infusion devices may be implanted in or otherwise connected to patients, to deliver medication at controlled intervals over a prolonged period of time. In some devices, when the batteries die, the devices are simply thrown away. Also, as the battery power supplies for such devices have limited capacities, some devices typically require multiple replacements of batteries over their operational life. There is a demand in the industry for infusion devices which make efficient use of power supplies and, thus, require fewer or no power supply replacements. This demand is particularly important for implantable devices, which may require surgical removal to replace depleted power supplies.

SUMMARY OF THE DISCLOSURE

Accordingly, embodiments of the present invention relate to infusion devices and drive mechanisms for infusion devices which address the above-mentioned industry demands.

Preferred embodiments of the invention relate to such devices and drive mechanisms configured for implantation in a patient's body. Configurations described herein allow the drive mechanism and, thus, the infusion device to have a relatively small thickness dimension, for example, to minimize trauma to the implant recipient (referred to herein as the patient).

Further preferred embodiments relate to such devices and drive mechanisms configured and operated to make highly efficient use of electrical power to prolong operational life.

Yet further preferred embodiments relate to such devices and drive mechanisms configured to deliver relatively precisely controlled volumes of infusion medium, within a relatively wide range of volumes, including relatively small volumes.

Yet further preferred embodiments relate to such devices and drive mechanisms configured to deliver sufficiently precise volumes of relatively high concentration infusion medium.

An infusion device according to an embodiment of the invention includes a generally disc-shaped housing made from a biocompatible and infusion medium compatible material. The infusion device housing contains a reservoir for holding a volume of infusion-medium, such as, but not limited to, a medication to be administered to the patient. The infusion device housing has an outlet through which the infusion medium may be expelled.

The infusion device further includes a drive mechanism having an inlet coupled in fluid flow communication with the reservoir and an outlet coupled in fluid flow communication with the infusion device housing outlet. In one embodiment, a filter may be disposed between the reservoir and the drive mechanism (or as part of the inlet of the drive mechanism). In a further embodiment, expandable and compressable devices, such as one or more volume compensators or accumulators, which may also be, for example, accumulators, also may be disposed in the flow path between the reseervoir and the drive mechanism inlet, to dampen surges and ebbs in the flow.

The drive mechanism employs electromagnetic and mechanical forces to move a piston between retracted and forward positions or states, to cause infusion medium to be drawn from the reservoir, through an inlet and forced out of an outlet. A drive mechanism, according to one embodiment, comprises an assembly of components which may be manufactured and assembled in a relatively cost efficient manner. The components include a housing containing a coil disposed within a coil cup, a piston channel surrounded by the coil, a piston extending through the piston channel, an armature disposed at one end of the piston channel and an outlet chamber with a valve assembly disposed at the other end of the piston channel.

When the coil is in a quiescent state, the armature and piston are urged toward a retracted position by mechanical or magnetic forces. When the coil is energized, the armature and piston move to a forward stroke position. The movement of the piston from a retracted position to a forward position creates pressure differentials within the drive mechanism to drive medium out the outlet. Mechanical force may return the piston to the retracted position. The movement of the piston from a forward position to a retracted position creates pressure differentials to draw medium into the drive mechanism inlet.

Embodiments of the invention employ a coaxial arrangement of the piston, the piston channel and the coil, to provide significant advantages with respect to providing a relatively thin form factor and efficient power usage. A number of features can each provide or be combined to contribute to a reduction in the thickness form factor of the drive mechanism. For example, a coaxial arrangement of components can be implemented with a smaller thickness form factor than alternative arrangements in which components are arranged in series with each other in the thickness dimension. Embodiments may include an inlet volume on one side of the coil and an outlet chamber on the opposite side of the coil, with a flow passage through the piston channel, such that the coil and flow channel share a common portion of the thickness dimension. The armature may be located within the inlet volume and, thus, share a common portion of the thickness dimension with the inlet volume. The outlet chamber may be centrally located within the same housing that has the coil cup and formed in relatively close proximity to the coil cup in the thickness dimension of the housing.

Further embodiments may include an outlet port and one or more fluid flow damping or accumulator structures, such as pillows or accumulators in pillow or accumulator cavities, in the housing, to help provide a relatively stable, constant output pressure during drive operations. The accumulator cavities, outlet port and outlet chamber may share a common portion of the thickness dimension of the drive mechanism, to maintain a relatively thin form factor.

In addition, a number of features described herein can provide, or be combined to contribute to, the efficient use of power to, prolong the operational life of the drive mechanism. One manner of improving the operational life of an infusion device according to embodiments of the present invention, is to lower the power consumption requirements of the drive mechanism by employing a coaxial coil and piston configuration and one or more features for making highly efficient use of electromagnetic energy. Another manner of improving the operational life of a device according to embodiments of the invention is to reduce the number of operations of the drive mechanism required over a given period of time, by pumping reduced volumes of a higher concentration infusion medium (an infusion medium with a higher concentration of active ingredients) or pumping higher concentration volumes at reduced intervals.

These and other aspects and advantages of the invention will be apparent to one of skill in the art from the accompanying detailed description and drawings.

BRIEF DESCRIPTION OF THE DRAWINGS

Referring now to the drawings in which like reference numbers represent corresponding parts throughout.

DETAILED DESCRIPTION OF PREFERRED EMBODIMENTS

The following detailed description is of the best presently contemplated mode of implementing the invention. This description is not to be taken in a limiting sense, but is made merely for the purpose of illustrating the general principles of embodiments of the invention. The scope of the invention is best defined by the appended claims.

As discussed above, the present invention relates generally to infusion devices having drive mechanisms and also to drive mechanism configurations for infusion of a medium into a patient or other environment. Preferred embodiments of the invention relate to such devices and drive mechanisms configured for implantation in a patient's body. Configurations described herein allow the drive mechanism and, thus, the infusion device to have a relatively small thickness dimension, for example, to minimize trauma to the implant recipient (referred to herein as the patient). Further preferred embodiments relate to such devices and drive mechanisms configured and operated to make highly efficient use of electrical power to prolong operational life.

Figure 1:
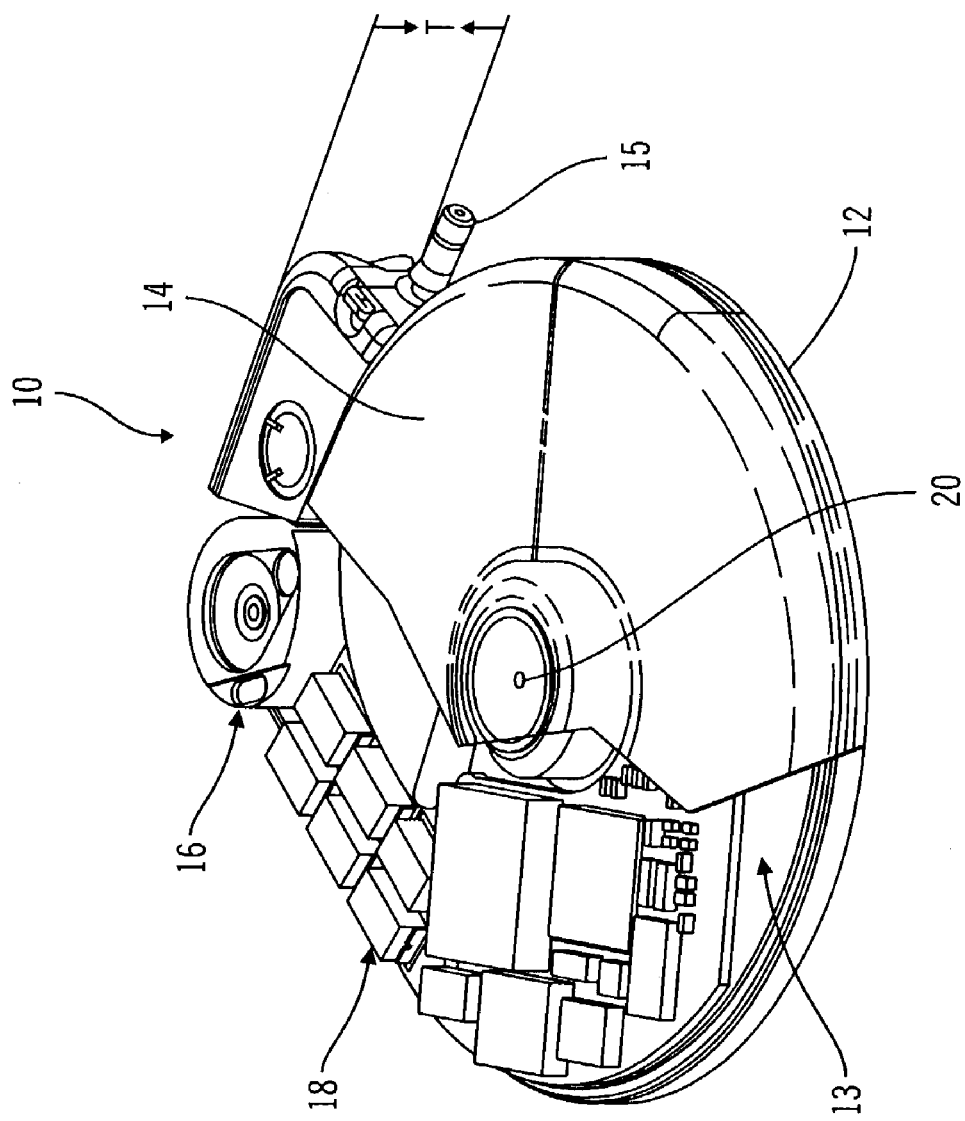
FIG. 1 is a perspective view of an implantable infusion device according to an embodiment of the invention.

FIG. 1 shows an implantable infusion device 10 according to an embodiment of the invention. The illustrated device 10 is configured to be surgically implanted into a patient, for example, in the abdominal region, between the skin and the abdominal wall. A catheter connected to the pump may deliver infusion medium to the patient, for example, by feeding infusion medium to a particular location in the venous system, within the spinal column or in the peritoneal cavity of the patient. As described below, preferred embodiments of the device 10 are configured in accordance with one or more aspects of the invention for enhancing implantability and prolonged usage once implanted. However, further embodiments of the invention may be implemented as external infusion devices, which connect to patients through suitable catheter devices or the like. Yet further embodiments of the invention may be used in other contexts, for delivery of a medium into other suitable environments. Therefore, for purposes of simplifying the present disclosure, the term "patient" is used herein to refer to the entity or environment in which an implantable device is implanted or to which an external device is connected, whether or not the implant or connection is carried out for medical purposes. Also, the term "infusion medium" is used herein to refer to any suitable medium delivered by the drive device.

The device 10 includes a generally disc-shaped housing 12. While a generally circular disc-shaped embodiment is illustrated in FIG. 1, it will be understood that further embodiments of the invention may employ housings of other shapes, including, but not limited to, oval, oblong, rectangular, or other curved or polygonal shapes. The housing 12 has a diameter dimension D, defining the diameter of the disc shape, and a maximum thickness dimension T, defining the maximum thickness of the device. In implantable device embodiments, the housing 12 is made of a biocompatible material and preferably has a relatively small or minimized thickness dimension T, to reduce or minimize patient trauma during implant surgery and after implantation.

The housing 12 includes a reservoir housing portion 13 containing a reservoir for holding a volume of infusion medium, such as, but not limited to, a liquid medication to be administered to the patient. The housing 12 includes a further housing portion 14, located above the reservoir housing portion 13 in the orientation shown in FIG. 1, for containing a drive mechanism, a power source and control electronics described below.

Representative examples of reservoir housing portions and reservoirs which may be employed in embodiments of the invention are described in co-pending U.S. patent application Ser. No. 60/317,880, titled "Infusion Device And Reservoir For Same," which is incorporated herein by reference. However, further embodiments may employ other suitable reservoir configurations, including, but not limited to, those described in U.S. Pat. No. 5,514,103 and U.S. Pat. No. 5,176,644, each to Srisathapat et al, U.S. Pat. No. 5,167,633 to Mann et al., U.S. Pat. No. 4,697,622 to Swift and U.S. Pat. No. 4,573,994 to Fischell et al.

The housing 12 also has an outlet 16 through which the infusion medium may be expelled. When the device 10 is implanted in a patient or connected externally to a patient, a catheter may be connected to the outlet 16, to deliver infusion medium expelled from the outlet 16 into the patient's blood stream or to a selected location in the patient's body. The infusion device 10 also includes an inlet structure 18 which provides a closeable and sealable fluid flow path to the reservoir in the reservoir portion 13 of the housing. The inlet structure provides a port for receiving a needle through which fluid may be transferred to the infusion device, for example, to fill or re-fill the reservoir of the device. In preferred embodiments, the inlet structure is configured to re-seal after a fill or re-fill operation, and to allow multiple re-fill and re-seal operations. One example of an inlet structure is described in co-pending U.S. patent application Ser. No. 60/318,056, titled "Infusion Device And Inlet For Same," which is incorporated herein by reference. However, further embodiments may employ other suitable inlet structures, including, but not limited to, those described in U.S. Pat. No. 5,514,103 and U.S. Pat. No. 5,176,644, each to Srisathapat et al, U.S. Pat. No. 5,167,633 to Mann et al., U.S. Pat. No. 4,697,622 to Swift and U.S. Pat. No. 4,573,994 to Fischell et al.

The infusion device 10 includes a drive mechanism 20, such as a pump, and an electronic control system 22 located in the housing portion 14. The drive mechanism 20 is connected between the reservoir and the outlet 16. The electronic control system 22 includes a power source, such as a battery, and control electronics for controlling the drive mechanism 20 to deliver infusion medium from the reservoir, to the patient in a selected manner. The drive mechanism may be controlled to deliver infusion medium in any suitable manner, for example, according to a programmed dispensing rate or schedule or according to an actuation signal from a sensor, timer or other suitable source.

In implantable embodiments, the portion 14 of the housing 12 that contains the drive mechanism 20 and control electronics 22 is preferably hermetically sealed from the external environment and from the reservoir housing portion 13, while the reservoir housing portion 13 may or may not be hermetically sealed. In preferred embodiments, both the portion 14 of the housing 12 and the reservoir housing portion 13 are hermetically sealed. In such an embodiment, the housing portion 14 containing the drive mechanism 20 and control electronics 22 may be made from titanium or titanium alloy or other biocompatible metals, while the reservoir portion 13 of the housing may be made from such metals or a biocompatible and infusion medium compatible plastic.

The drive mechanism 20 includes mechanical and electromagnetic components that inherently inhabit a volume of space within the housing portion 14 in which the components reside and operate. In that regard, the drive mechanism 20 can contribute to the thickness requirements of the housing portion 14 and, thus, to the overall thickness dimension T of the device 10. Preferred embodiments of the present invention relate to and employ drive mechanism configurations that reduce or minimize the thickness requirements of the device, without compromising drive capabilities.

The ability to reduce or minimize the device thickness dimension T, without compromising the drive capabilities, can provide significant advantages with respect to patient comfort, appearance and flexibility in selecting implant locations in the body. Accordingly, drive mechanism configurations that allow for reduced or minimized device thickness dimensions, as described herein, can provide significant advantages in the implantable infusion device technology. Thus, in preferred embodiments, the drive mechanism 20 is configured with one or more features described herein that provide a relatively small or minimal thickness and allow the device 10 to have a relative small or minimal thickness T.

Also in preferred embodiments, the device 10 is configured such that, once implanted, it functions for a relatively long period of time to administer infusion medium to the patient and periodically be replenished from outside of the patient's body. The operational life of the device 10 is, however, limited in part by the capacity of its power source and the power requirements of the device. Preferred embodiments of the device 10 employ drive mechanisms, as described below, that provide reliable pumping action and are highly efficient with respect to power consumption, to improve the operational life of the device 10. Alternatively or in addition, drive mechanisms that provide highly efficient use of power, as described below, may be operated with smaller power sources (for example, smaller batteries) which can allow the device 10 to be made smaller.

One manner of lowering the power consumption requirements of the device 10 is to employ a coaxial coil and piston pump configuration and one or more features described herein for making highly efficient use of electromagnetic energy. Another manner of lowering the power consumption requirements of the device 10 is to reduce the number of operations of the drive mechanism 20 required over a given period of time, by pumping reduced volumes of a higher concentration infusion medium (an infusion medium with a higher concentration of active ingredients) or pumping higher concentration volumes at reduced intervals. However, higher concentration mediums may require a greater precision in controlling the volume delivered to the patient during a drive operation, to avoid delivering too great or too small of a volume of the higher concentration medium to the patient. Accordingly further preferred drive mechanisms 20 are configured with one or more features described herein to allow delivery of controlled volumes of infusion medium and, thus, to allow sufficiently precise delivery of relatively high concentration infusion medium.

First Drive Mechanism Embodiment

Figure 2:
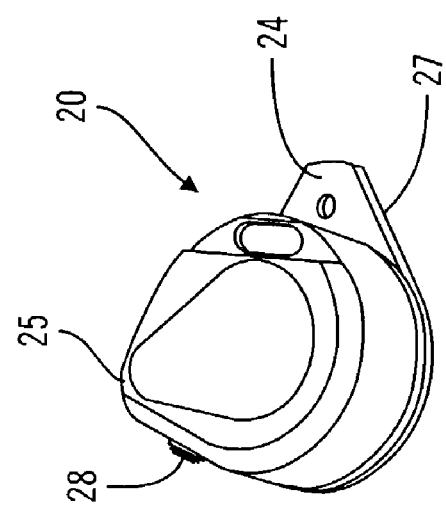
FIG. 2 is a perspective view of a drive mechanism for an implantable infusion device according to an embodiment of the invention.

FIG. 2 shows a drive mechanism 20 according to one example embodiment of the present invention. In the illustrated embodiment, the drive mechanism 20 has a partially cylindrical, disc-shaped configuration with extended corners 24 and 25. An inlet 27 is provided at the corner 24 and an outlet 28 is provided at the corner 25. The inlet 27 may be connected in flow communication with the reservoir portion 13 of the device 10 in FIG. 1, though suitable conduit (not shown) within the device 10. Similarly, the outlet 28 may be connected in flow communication with the outlet 16 of the device 10 in FIG. 1, through suitable conduit (not shown) within the device 10.

Figure 3:
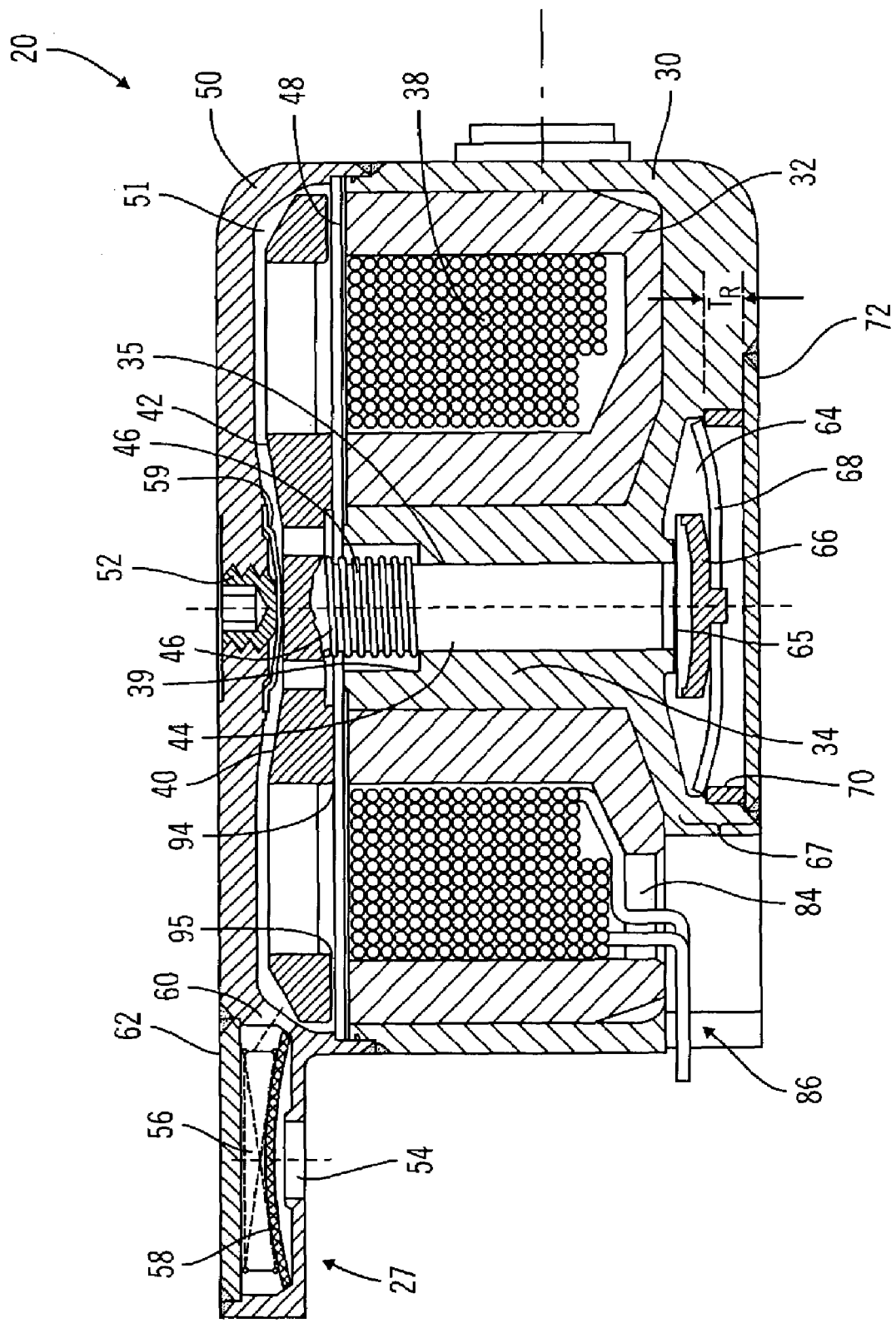
FIG. 3 is a cross-section view of one example embodiment of the drive mechanism of FIG. 2, in a retracted position or state.
Figure 4:
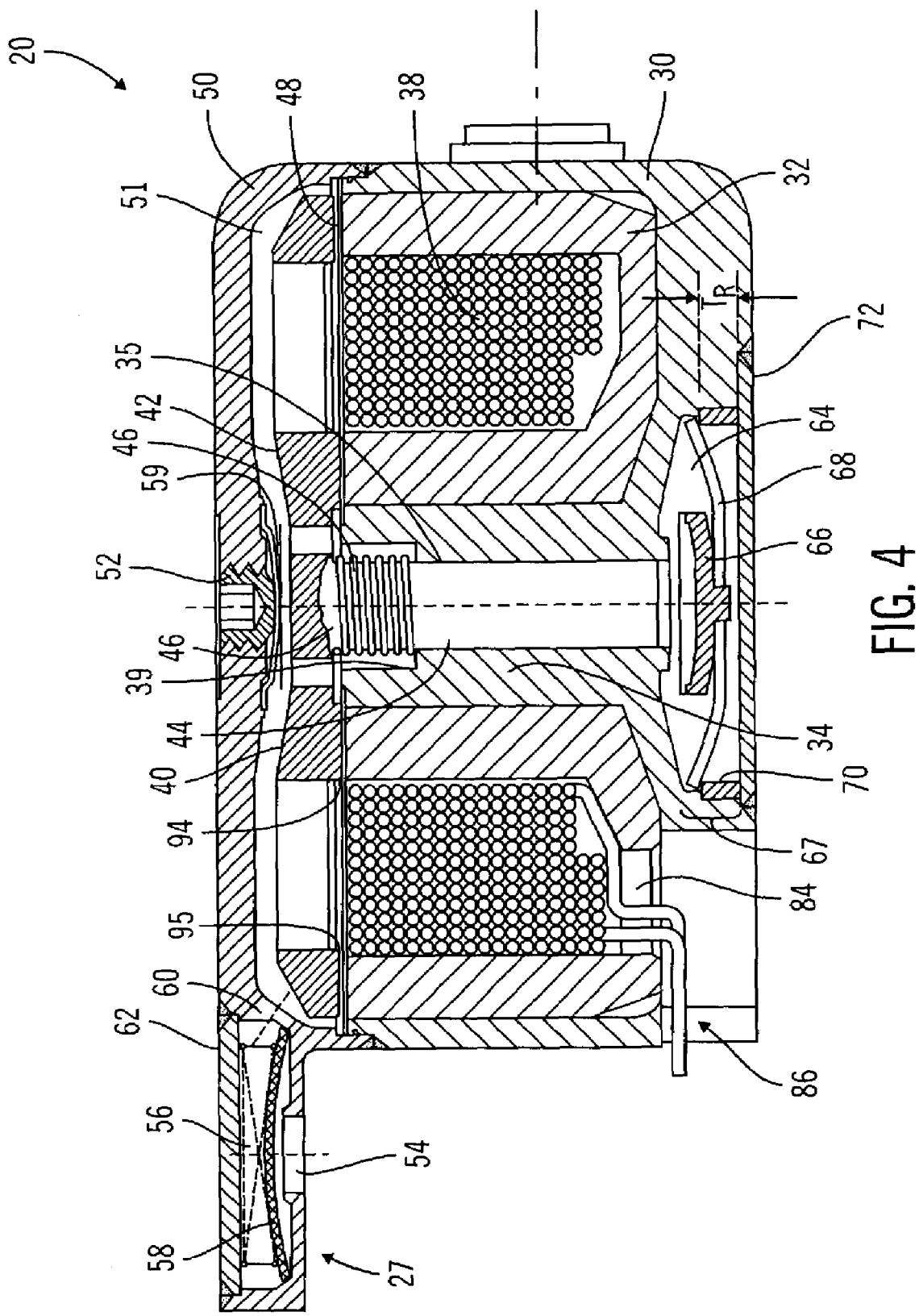
FIG. 4 is a cross-section view of the example drive mechanism embodiment of FIG. 3, in a forward stroke position or state.

FIG. 3 shows a cross-sectional view of an embodiment of a drive mechanism 20, in a retracted position or state. FIG. 4 shows a cross-sectional view of the same drive mechanism 20 embodiment, in a forward position or state. As described in more detail below, the drive mechanism 20 employs electromagnetic and mechanical forces to change (or move) between retracted and forward states, to cause infusion medium to be drawn in through the inlet 27 and forced out of the outlet 28. The drive mechanism 20, according to one embodiment, comprises an assembly of components as shown in an exploded view in FIG. 5. Some of these components are also shown in perspective views in FIGS. 6–10.

Figure 6:
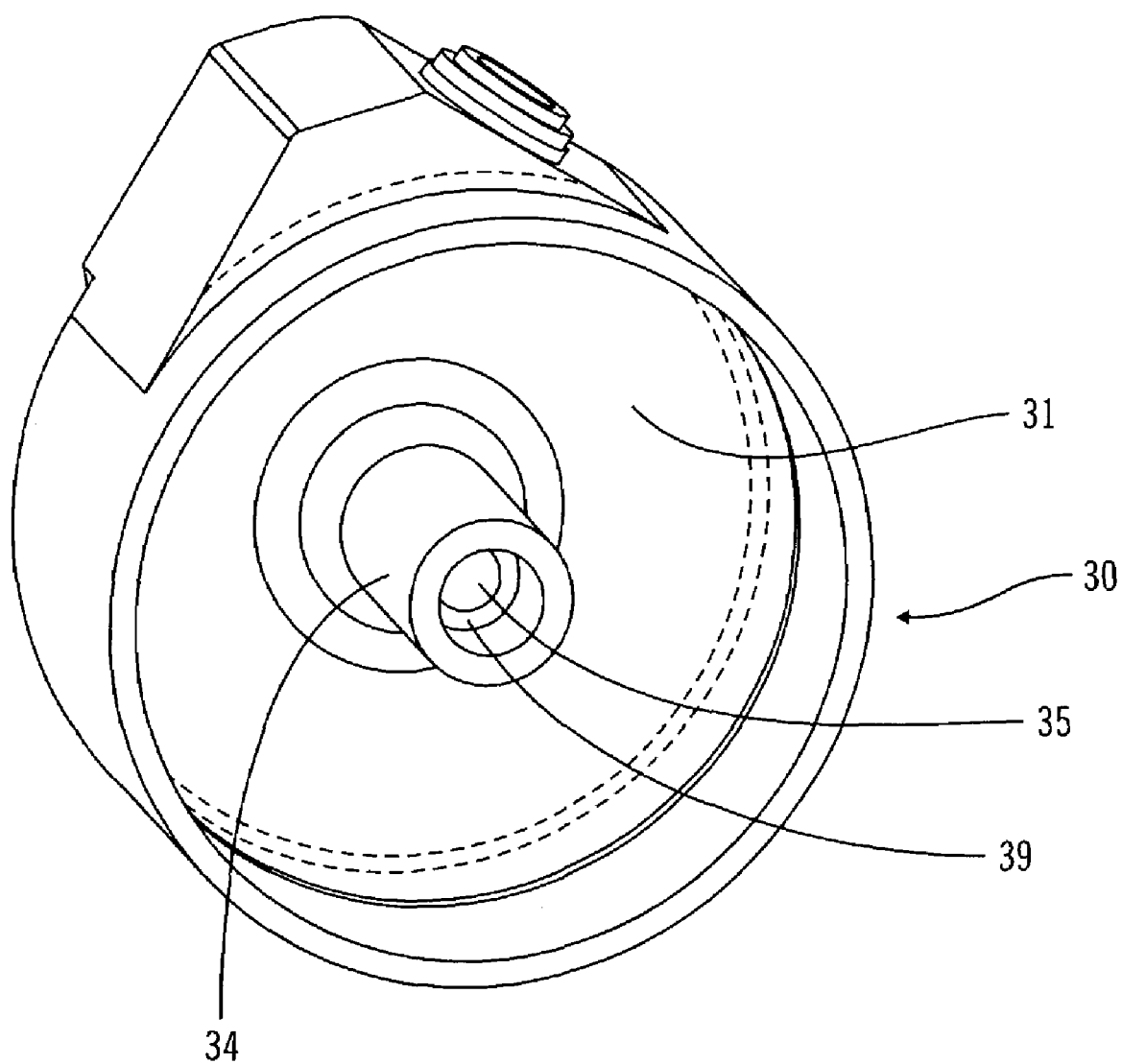
FIG. 6 is a perspective view of an embodiment of the inlet end of a housing for the drive mechanism in FIGS. 3 and 4.
Figure 7:
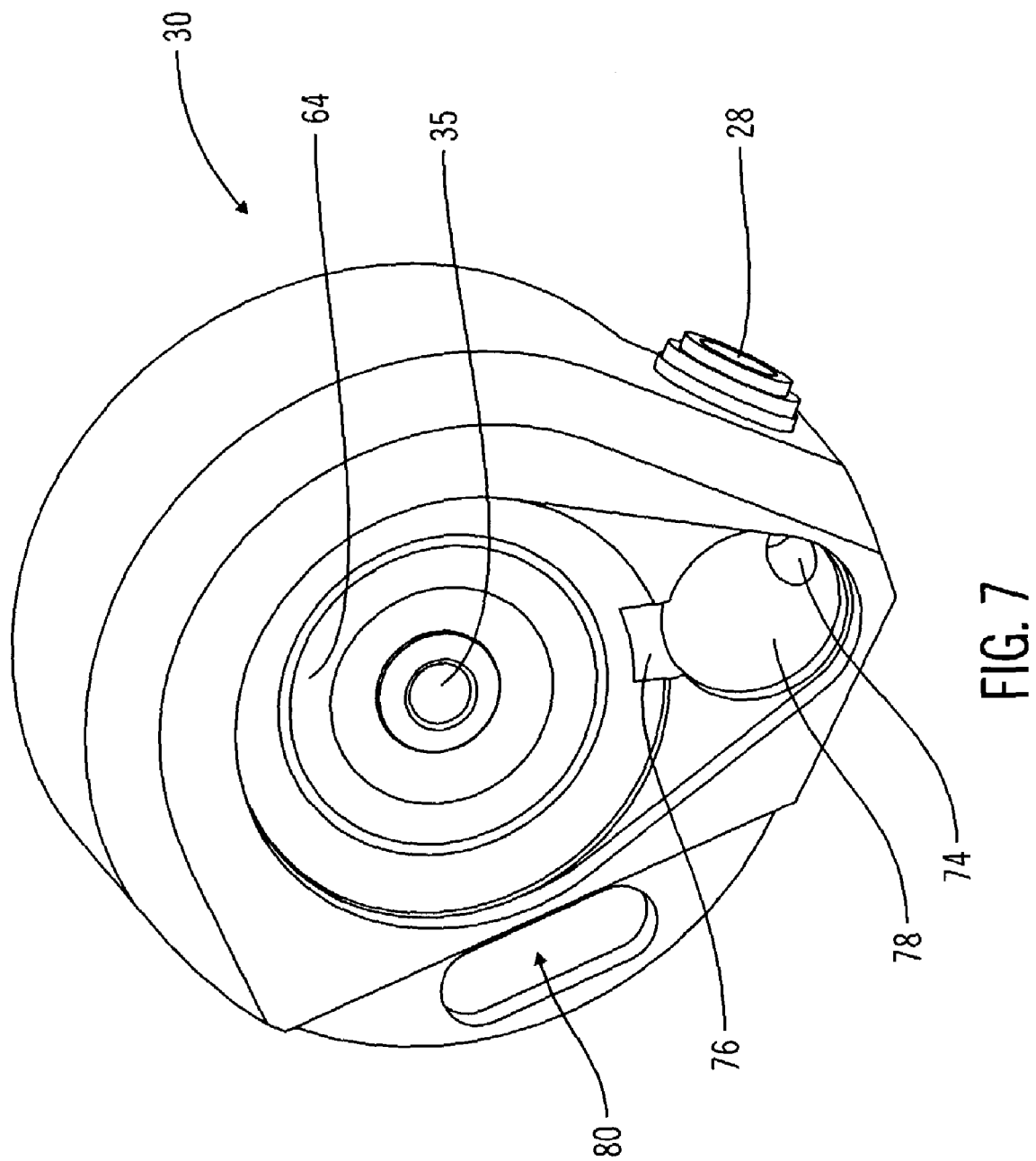
FIG. 7 is a perspective view of an embodiment of the outlet end of the drive mechanism housing of FIG. 6.

With reference to those drawings, the drive mechanism 20 includes a housing member 30 that is open on one side to a hollow, annular interior section 31. FIGS. 6 and 7 show two perspective views of the housing 30. The housing member 30 has a central hub portion 34 with a central piston channel 35. The bottom side of the housing member 30 (with reference to the orientation shown in FIGS. 3 and 4), includes an opening to the hollow interior section 31 through which coil wires may pass, as described below. The bottom side of the housing member also includes a configuration of recesses and cavities for providing an outlet chamber, an outlet passage and, in some embodiments, accumulator chambers as described below. The housing member 30 is preferably made of a generally rigid, biocompatible and infusion medium compatible material, having no or low magnetic permeability such as, but not limited to, titanium, stainless steel (which may be ferritic or non-ferritic), biocompatible plastic, ceramic, glass or the like.

Figure 8:
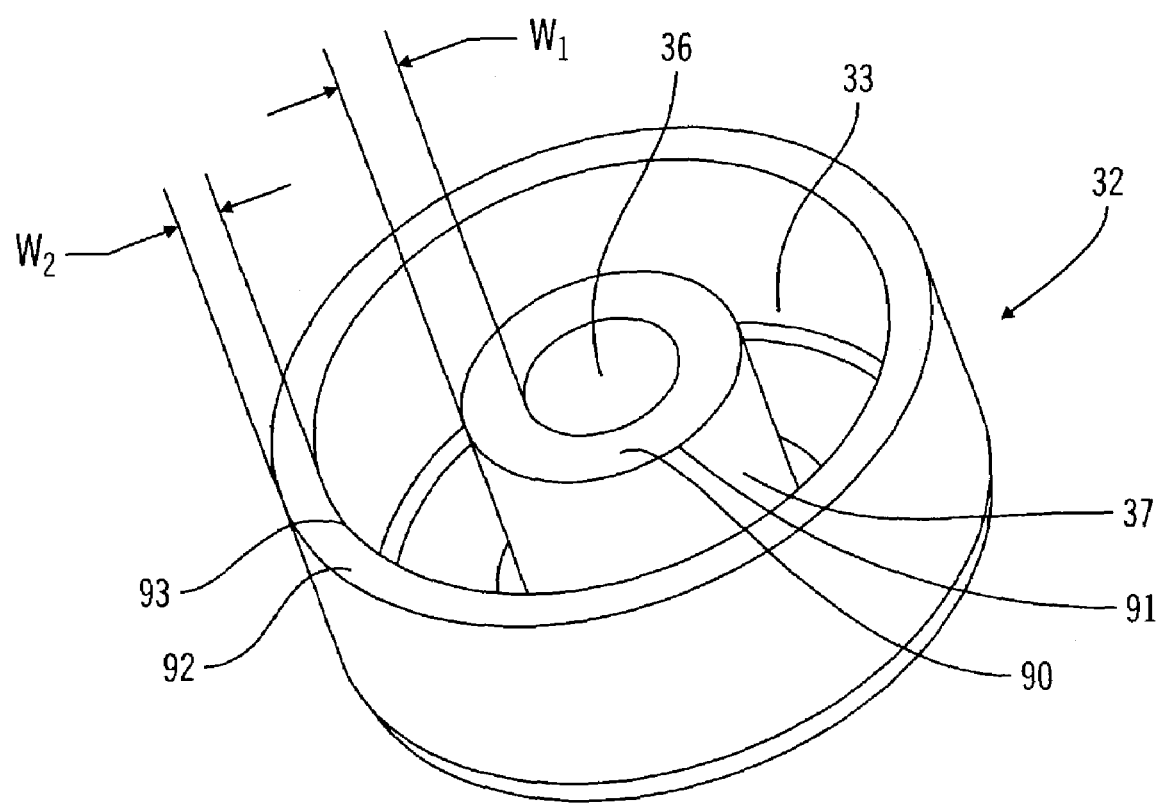
FIG. 8 is a perspective view of an embodiment of a coil cup for the drive mechanism in FIGS. 3 and 4.

As shown in FIGS. 3 and 4, a coil cup 32 is located within the annular interior section of the housing 30. A perspective view of the coil cup 32 is shown in FIG. 8. The coil cup 32 has a generally cylinder shape, open on one side to a hollow, annular interior 33. The coil cup includes an open piston channel or bore 36 located in a central hub portion 37, axial relative to the annular interior. The hub portion 37 of the cup member defines an inner annular wall 90 having an end surface 91 (or inner pole surface) of width $W_1$. The cup member has an outer wall 92 having an end surface 93 (or outer pole surface) of a width $W_2$. The outer wall 92 is connected to the inner wall 90 or hub portion 37 by a backiron portion of the cup member. As described in further detail below, at the open end of the cup member, the end surfaces 91 and 93 of the inner and outer walls 90 and 92 define pole surfaces that cooperate with pole surfaces on an armature to provide a magnetic return path structure for electromagnetic flux during a forward stroke of the drive mechanism. In preferred embodiments, the width $W_1$ of inner pole surface 91 is greater than the width $W_2$ of the outer pole surface 93, to provide certain electromagnetic characteristics as described below.

When assembled, the coil cup is located in the hollow interior of the housing member 30, with the central portion 34 of the housing 30 extending through the piston channel 36 of the coil cup 32, as shown in FIGS. 3 and 4. A coil 38 is located within the hollow, annular interior of the coil cup 32, and is disposed around the axis A of the annular interior of the coil cup 32. The coil cup 32 is provided with an opening 84, through which coil leads extend, as shown in FIGS. 3 and 4. The coil cup 32 is preferably made of a generally rigid material, having a relatively high magnetic permeability such as, but not limited to, low carbon steel, iron, nickle, ferritic stainless steel, ferrite, other ferrous materials, or the like. The coil 38 comprises a conductive wire wound in a coil configuration. The coil wire may comprise any suitable conductive material such as, but not limited to, silver, copper, gold or the like, with each turn electrically insulated from adjacent turns and the housing. In one preferred embodiment, the coil wire has a square or rectangular cross-section, to allow minimal space between windings, thereby to allow a greater number of coil turns and, thus, improved electrical efficiency.

Figure 9:
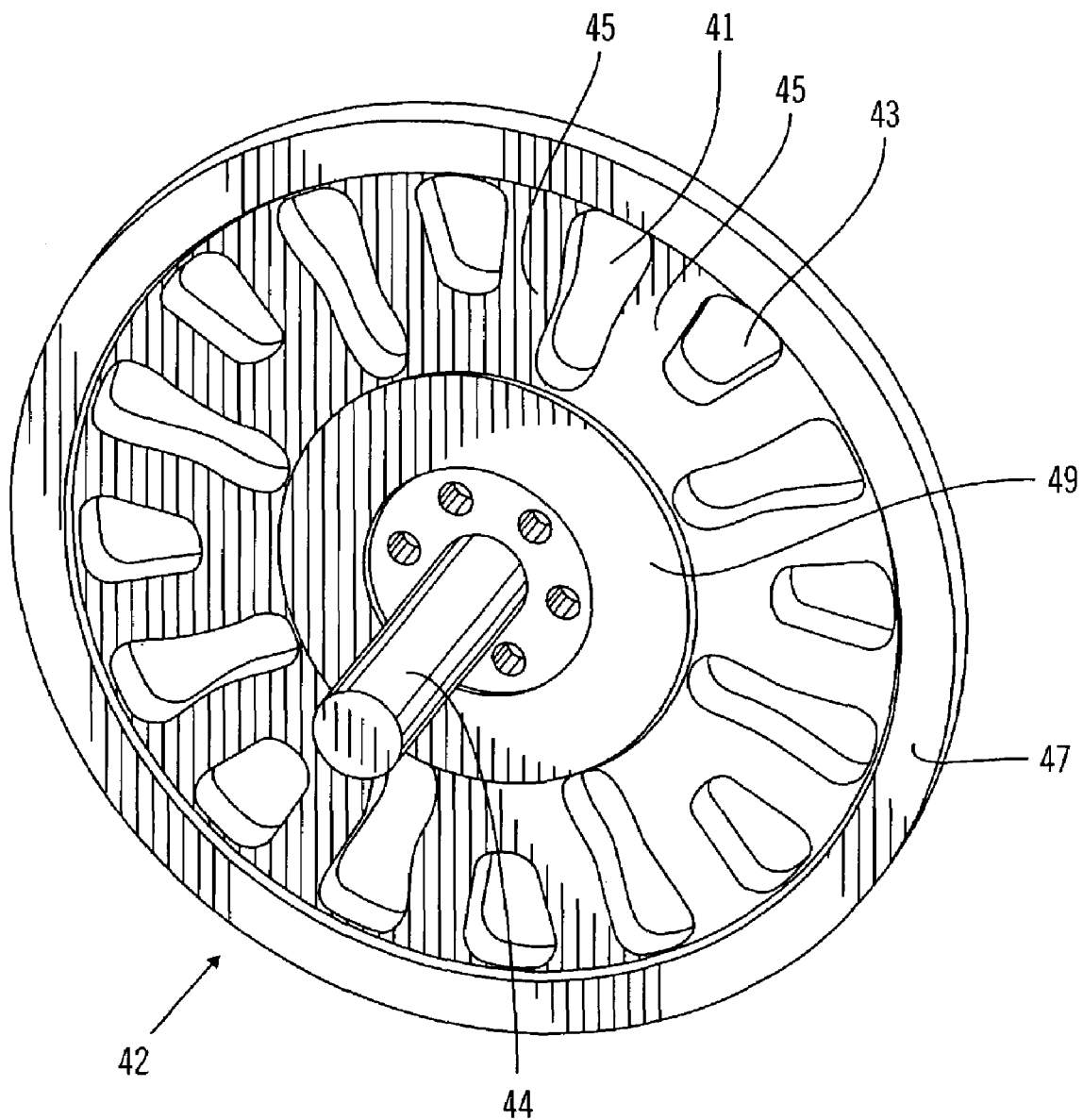
FIG. 9 is a perspective view of an embodiment of an actuator comprising an armature and a piston for the drive mechanism in FIGS. 3 and 4.

The drive mechanism 20 also includes an actuator member 40, which has an armature portion 42 and a piston portion 44. The actuator member is preferably made of a generally rigid, biocompatible and infusion medium compatible material, having a relatively high magnetic permeability such as, but not limited to, ferrous materials, ferritic stainless steel with high corrosion resistance, or the like. In the embodiment of FIGS. 3, 4 and 9, the actuator (with an armature portion 42 and a piston portion 44) is formed as a single, unitary structure. In other embodiments as described below, the piston portion may be a separate structure with respect to the armature portion.

A perspective view of an example actuator member 40 is shown in FIG. 9, wherein the armature portion 42 of the actuator member has a round, disc shape, provided with at least one opening and, preferably, a plurality of openings as shown in the drawing. The openings in the illustrated example include a plurality of larger openings 41 which are elongated in the radial dimension of the armature, and a plurality of smaller openings 43, each disposed between a pair of larger openings 41. The sections 45 of the armature 42 between the openings 41 and 43 define radial struts coupling an annular outer section (or outer pole) 47 to an inner section (or inner pole) 49 of the armature. In preferred embodiments, the width $W_1$ of the inner pole surface 49 is greater than the width $W_2$ of the outer pole surface 47, corresponding to the difference between the width of the pole surface 91 on the inner wall 90 of the cup member and the width of the pole surface 93 on the outer wall 92 of the cup member.

As described in more detail below, the armature 42 cooperates with the inner and outer walls of the coil cup 32, to provide a flux path for electromagnetic flux. The spacing between the pole surfaces on the armature 42 and the pole surfaces on the coil cup walls define gaps in the flux path. In preferred embodiments, the spacing between the outer pole surface 47 of the armature 42 and the outer pole surface 93 of the outer wall 92 of the coil cup 32 (or the barrier 48) is greater than the spacing between the inner pole surface 49 of the armature and the pole surface 91 of the inner wall 90 of the coil cup (or the barrier 48), when the actuator is in the retracted position shown in FIG. 3. A greater outer pole spacing, relative to the inner pole spacing, can result in reduced residual flux that could otherwise cause the armature to stick in the forward position (the FIG. 4 position). In addition, a greater outer pole spacing reduces the squeezing effect on infusion medium between the outer pole of the armature 42 and the barrier 48, as the armature 42 moves toward the forward position during actuation of the pump mechanism.

The radial struts 45 in the armature provide radial paths for electromagnetic flux between the outer and inner pole sections 47 and 49 of the armature. The openings 41 and 43 provide a passage for infusion medium to pass, as the actuator 40 is moved between retracted and forward stroke positions, to reduce resistance to the actuator motion that the infusion medium may otherwise produce. In the embodiment illustrated in FIG. 9, additional openings are provided around the piston portion 44, to provide additional flow paths for infusion medium to pass. The configuration of openings is preferably designed to provide a sufficient conductor for electromagnetic flux and, yet minimize or reduce viscous resistance to actuator motion. To further reduce viscous resistance during actuator motion in the forward stroke direction, the inner and outer pole sections 47 and 49 may have textured surfaces facing the coil cup 38, to provide flow areas for medium between the pole sections 47, 49 and the coil cup 38 (or barrier 48 described below).

With reference to FIGS. 3 and 4, the actuator member 40 is arranged with the piston portion 44 extending through the axial channel 35 of the housing 30 and with the armature portion 42 positioned adjacent the open side of the coil cup 32. An actuator spring 46 is positioned to force the armature portion 42 of the actuator 40 in the direction away from the open side of the coil cup 32, to provide a gap between the armature 42 and the open side of the coil cup 32. A biocompatible and infusion medium compatible barrier 48 is located over the open side of the coil cup 32, between the armature 42 and the coil cup 32, to maintain a gap between those two members and/or to help seal the annular interior of the coil cup and coil 38. In other embodiments in which infusion medium may contact the coil, the barrier 48 may be omitted.

The actuator spring 46 in the illustrated embodiment comprises a coil spring disposed around the piston portion 44 of the actuator 40, adjacent the armature portion 42. One end of the coil spring abuts the armature portion 42 of the actuator, while the opposite end of the coil spring abuts a shoulder 39 in the piston channel 35 of the housing 30. In this manner, the actuator spring 46 imparts a spring force between the housing and the actuator 40, to urge the actuator toward its retracted position shown in FIG. 3.

In the illustrated embodiment, by using a coil spring 46 located around and coaxial with the piston portion 44 and disposed partially within the piston channel 35, the actuator spring may have minimal or no contribution to the overall thickness dimension of the drive mechanism. However, in other embodiments, actuator springs may have other suitable forms and may be located in other positions suitable for urging the actuator toward its retracted position shown in FIG. 3. The actuator spring 46 is preferably made of a biocompatible and infusion medium compatible material that exhibits a suitable spring force such as, but not limited to, titanium, stainless steel, MP35N cobalt steel or the like.

The drive mechanism 20 further includes a cover member 50 which attaches to the housing member 30, over the open side of the housing member and the barrier 48. The cover member 50 is preferably made of a generally rigid, biocompatible and infusion medium compatible material, having a relatively low magnetic permeability (being relatively magnetically opaque) such as, but not limited to, titanium, stainless steel, biocompatible plastic, ceramic, glass or the like.

The cover member 50 defines an interior volume 51 between the barrier 48 and the inner surface of the cover member. The armature portion 42 of the actuator member 40 resides within the interior volume 51 when the cover is attached to the housing, as shown in FIGS. 3 and 4. As described below, the armature 42 is moveable in the axial direction A within the volume 51, between a retracted position shown in FIG. 3 and a forward stroke position shown in FIG. 4. This movement is created by the action of electromagnetic force generated when a current is passed through the coil 38 and the mechanical return action of the actuator spring 46.

An adjusting plunger 52 is located within the cover 50, for contacting the armature 42 when the armature is in the fully retracted position shown in FIG. 3, to set the retracted or retracted position of the armature. In preferred embodiments, a seal may be disposed between the plunger 52 and the cover member 50, for example, but not limited to, a silicon rubber sealing ring. In further embodiments, a flexible diaphragm 59 (such as, but not limited to, a thin titanium sheet or foil) may be coupled to the inside surface of the cover 50 and sealed around the opening through which the plunger 52 extends. The diaphragm will flex to allow the plunger to define an adjustable retracted position and, yet, provide sealing functions for inhibiting leakage at the interface between the plunger 52 and the cover 50. In further preferred embodiments, once a proper armature position is set, the plunger is fixed in place with respect to the cover member, for example, by adhering the plunger to the cover member with one or more welds, adhesives or other securing methods.

The cover member 50 includes the inlet 27 of the drive mechanism, which has an inlet opening 54 in fluid flow communication with the interior volume 51, as described below. The inlet opening 54 connects in fluid flow communication with the reservoir of the infusion device 10 (FIG. 1), to receive infusion medium from the reservoir. Connection of the inlet opening 54 and the reservoir may be through suitable conduit (not shown), such as tubing made of suitable infusion medium compatible material, including, but not limited to titaniaum, stainless steel, biocompatible plasitc, ceramic, glass or the like.

The inlet opening 54 provides a flow path to an inlet chamber 56 formed in the cover member 50, adjacent the inlet opening. A filter or screen member, such as a porous or screen material 58, may be disposed within the inlet chamber 56. The filter or screen member 58 is provided in a flow path between the inlet opening 54 and an inlet port 60 to the volume 51. A one-way inlet valve (not shown), to allow medium to flow into but not out of the interior volume 51 through the inlet, may also be provided in the flow path between the inlet opening 54 and the inlet port 60, or within the inlet port 60. The cover member 50 may be provided with an inlet cover 62 that, when removed, allows access to the inlet chamber 56 to, for example, install, replace or service a filter 58 or inlet valve, or to service or clean the inlet 27. However, in one preferred embodiment, an inlet valve is omitted and, instead, the drive mechanism 20 is configured as a single valve mechanism, employing a single outlet valve (for example, outlet valve assembly 67 described below) and no inlet valve.

As shown in FIGS. 3 and 4, the piston portion 44 of the actuator 40 extends through the axial channel 35 in the housing 30, toward an outlet chamber 64 at the end of the axial channel 35. The channel 35 has an inside diameter which is larger than the outside diameter of the piston portion 44. As a result, an annular volume is defined between the piston portion 44 and the wall of the axial channel 35, along the length of the axial channel 35. Infusion medium may flow through the annular volume, from the volume 51 within the cover 50 to a piston chamber 65 located between the free end of the piston portion 44 and a valve member 66 of a valve assembly 67. In preferred embodiments, the radial spacing between the piston portion 44 and the wall of the channel 35 is selected to be large enough to provide a suitable flow toward the piston chamber 65 to refill the piston chamber 65 (during a return stroke of the piston portion), but small enough to sufficiently inhibit back flow of medium from the piston chamber 65 (during a forward stroke of the piston portion).

The actual radial spacing between the piston portion 44 and the wall of the channel 35 to achieve such results depends, in part, on the overall dimensions of those components, the pressure differentials created in the mechanism and the viscosity of the infusion medium. In preferred embodiments, the radial spacing is selected such that the volume of medium for refilling is between about 1 and 4 orders of magnitude (and, more preferably, about 2 orders of magnitude) greater than the volume of medium that back-flows through the space. Alternatively, or in addition, the radial spacing may be defined by the ratio of the diameter $D_P$ of the piston portion 44 the diameter Dc of the channel 35, where the ratio $D_P/D_C$ is preferably within a range of about 0.990 to about 0.995. As a representative example, a total spacing of about 400 to 600 micro-inches and, preferably, an average radial gap of about 250 micro-inches annularly around the piston portion 44 may be employed.

The valve assembly 67 in the embodiment of FIGS. 3 and 4 includes the valve member 66, a valve spring 68 and support ring 70. The valve member 66 is located within the outlet chamber 64 and, as shown in FIG. 3, is positioned to close the opening between the axial channel 35 and the outlet chamber 64, when the actuator 40 is in the retracted position. In FIG. 4, the valve member 66 is positioned to open a flow passage between the axial channel 35 and the outlet chamber 64. The valve spring 68 is located within the outlet chamber 64, to support the valve member 66. The spring 68 imparts a spring force on the valve member 66, in the direction toward piston 44, urging the valve member 66 toward a closed position, to block the opening between the axial channel 35 and the outlet chamber 64.

The valve member 66 is preferably made of a generally rigid, biocompatible and infusion medium compatible material, such as, but not limited to, titanium, stainless steel, biocompatible plastic, ceramic, glass, gold, platinum or the like. A layer of silicon rubber or other suitable material may be attached to the rigid valve member material, on the surface facing the channel 35, to help seal the opening to the channel 35 when the valve member is in the closed position shown in FIG. 3.

The valve spring 68 is preferably made of a biocompatible and infusion medium compatible material that exhibits a suitable spring force such as, but not limited to, titanium, stainless steel, MP35N cobalt steel or the like. In the illustrated embodiment, the valve spring 68 has a generally flat, radial or spiral configuration. In preferred embodiments, the spring 68 includes radial arms that contact the interior of the outlet chamber in multiple locations around the periphery of the spring, to inhibit lateral or radial motion and improve stability of the spring. In further embodiments, a conical or belleville spring may be used. In yet further embodiments, other suitable valve spring configurations may be employed, including, but not limited to helical, conical, barrel, hourglass, constant or variable pitch springs or the like.

In the embodiment of FIGS. 3 and 4, the valve spring 68 is spaced from a valve cover 72 by the ring 70. The valve cover 72 is sealed to the housing 30, to enclose the outlet chamber 64. The ring 70 is disposed within the outlet chamber 64, between the spring 68 and the valve cover 72. With the valve member 66 supported between the spring 68 and the opening to the channel 35, the force imparted by the spring on the valve member is dependent, in part, on the characteristics and parameters of the spring and, in part, on the position of the spring within the outlet chamber. The ring 70 and the valve cover 72 are each preferably made of a generally rigid, biocompatible and infusion medium compatible material, such as, but not limited to, titanium, stainless steel, biocompatible plastic, ceramic, glass, gold, platinum or the like.

The thickness dimension $T_R$ of the ring 70 may be matched to fit within a recess within the outlet chamber, as shown in FIGS. 3 and 4. Alternatively, the thickness dimension $T_R$ of the ring 70 may be selected to define the position of the spring 68 within the outlet chamber, by defining the distance of the spring 68 relative to the valve cover 72 and relative to the opening between the axial channel 35 and the outlet chamber 64. A larger ring thickness $T_R$ will space the spring further from the valve cover 72 and closer to the opening to the axial channel 35, while a smaller ring thickness $T_R$ will space the spring closer to the valve cover 72 and further from the opening to the axial channel 35. In this manner, for a given spring 68, the force imparted by the spring on the valve member 66 to close the opening to the axial channel 35 (as shown in FIG. 3) may be selected or adjusted by selecting or adjusting the ring thickness $T_R$. The ring thickness $T_R$ and the spring characteristics are preferably selected to provide sufficient force to urge the valve member 66 into a suitably sealed or closed position as shown in FIG. 3, yet allow the movement force of the piston portion 44 (caused by electromagnetic force generated by the coil) to overcome the spring force and open the valve member 66 as shown in FIG. 4.

In the illustrated embodiment, the outlet chamber 64 comprises a cavity in the bottom of the housing 30, as shown in FIGS. 3, 4 and 7. Thus, in the illustrated embodiment, the outlet chamber cavity is generally centered within the same housing 30 that has the cavity holding the coil cup 32 and coil 38. With such an arrangement, the configuration of the drive mechanism 20 may be made with a relatively small thickness dimension (height dimension in the orientation shown in FIGS. 3 and 4) without compromising structural strength, as compared to alternative configurations in which the outlet chamber is formed with a separate member coupled to the housing 30.

As shown in FIG. 7, the outlet chamber cavity 64 may be provided in flow communication with an outlet 28 through a flow passage 74 and one or more accumulator cavities 78. The flow passage 74 comprises a channel which leads to the outlet 28 of the drive mechanism 20 and, eventually, to the device outlet 16 (FIG. 1). The outlet chamber cavity 64, flow passage 76, accumulator cavities 78 and flow passage 74 provide a flow path for infusion medium to flow from the outlet chamber to the device outlet 16, under pressure induced by operation of the drive mechanism 20. As shown in FIG. 7, the accumulator cavities 78, flow passage 76 and flow passage 74 may be provided lateral to the outlet chamber cavity 64 in the housing 30 to, thus, have minimal or no additional contribution to the overall thickness dimension T of the drive mechanism than that already required by the outlet chamber cavity 64.

Each accumulator cavity 78 forms a chamber which may contain one or more flexible, sealed packets, or accumulators, containing a compressible medium. In one preferred embodiment, each accumulator preferably comprises a packet made of a biocompatible and infusion medium compatible material of sufficient strength and flexibility to compress and expand under varying fluid pressures, such as, but not limited to stainless steel, titanium, platinum, which contains a compressible medium, such as, but not limited to a noble gas, such as argon or neon, or other suitable materials and media that provide a return pressure over a broad range of compression pressures. The accumulators may be used to help stabilize the flow rate of the drive mechanism and provide a relatively constant output pressure during drive operations, by acting as damping structures within the flow path between the outlet chamber 64 and the outlet 28. In addition, the accumulators may minimize backflow down axial channel 35 while the valve is closing or even prior to the vavle closing.

Figure 10:
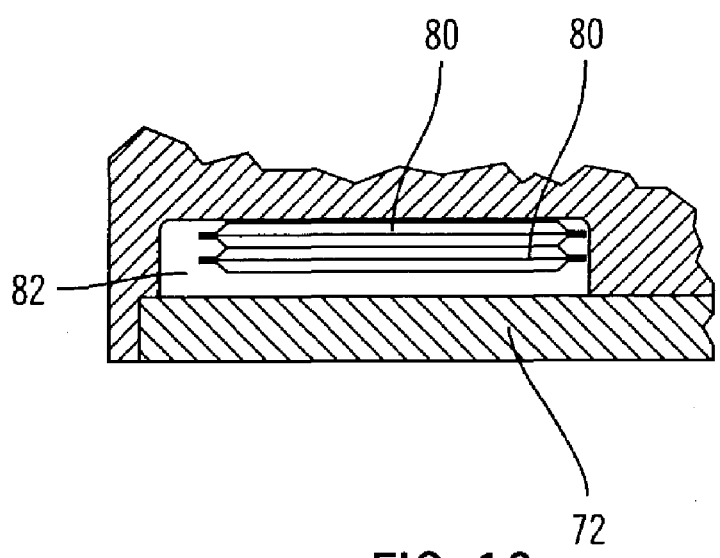
FIG. 10 is a partial cross-section view of a portion of a drive mechanism housing with an accumulator chamber.

For example, as shown in FIG. 10, one or more disc-shaped accumulators 80 may be stacked within each accumulator cavity, with or without an additional volume 82 for infusion medium. As the pressure of the infusion medium within the accumulator cavity increases, the accumulators 80 compress to increase the volume 82. Similarly, as the infusion medium pressure decreases, the accumulators 80 may expand and decrease the volume 82. In this manner, the accumulators 80 inhibit sharp changes in infusion medium pressure and provide a dampening mechanism for dampening pressure changes to allow a relatively constant pressure flow through the outlet 28, during operation of the drive mechanism 20. While the illustrated embodiment employs two accumulator cavities, each having two accumulators, other embodiments may employ any suitable number of accumulator cavities and accumulators. Other embodiments may employ cavities 78, without accumulators or with other mechanisms that provide volume adjustment or flow smoothing capabilities, including, but not limited to, bellows structures, sponge-type structures, fluid accumulators or the like. Yet other embodiments, in which the maintenance of a relatively constant outlet pressure is not a concern, may omit accumulator cavities and accumulators, such that the outlet chamber is directly coupled to the outlet port.

Figure 5:
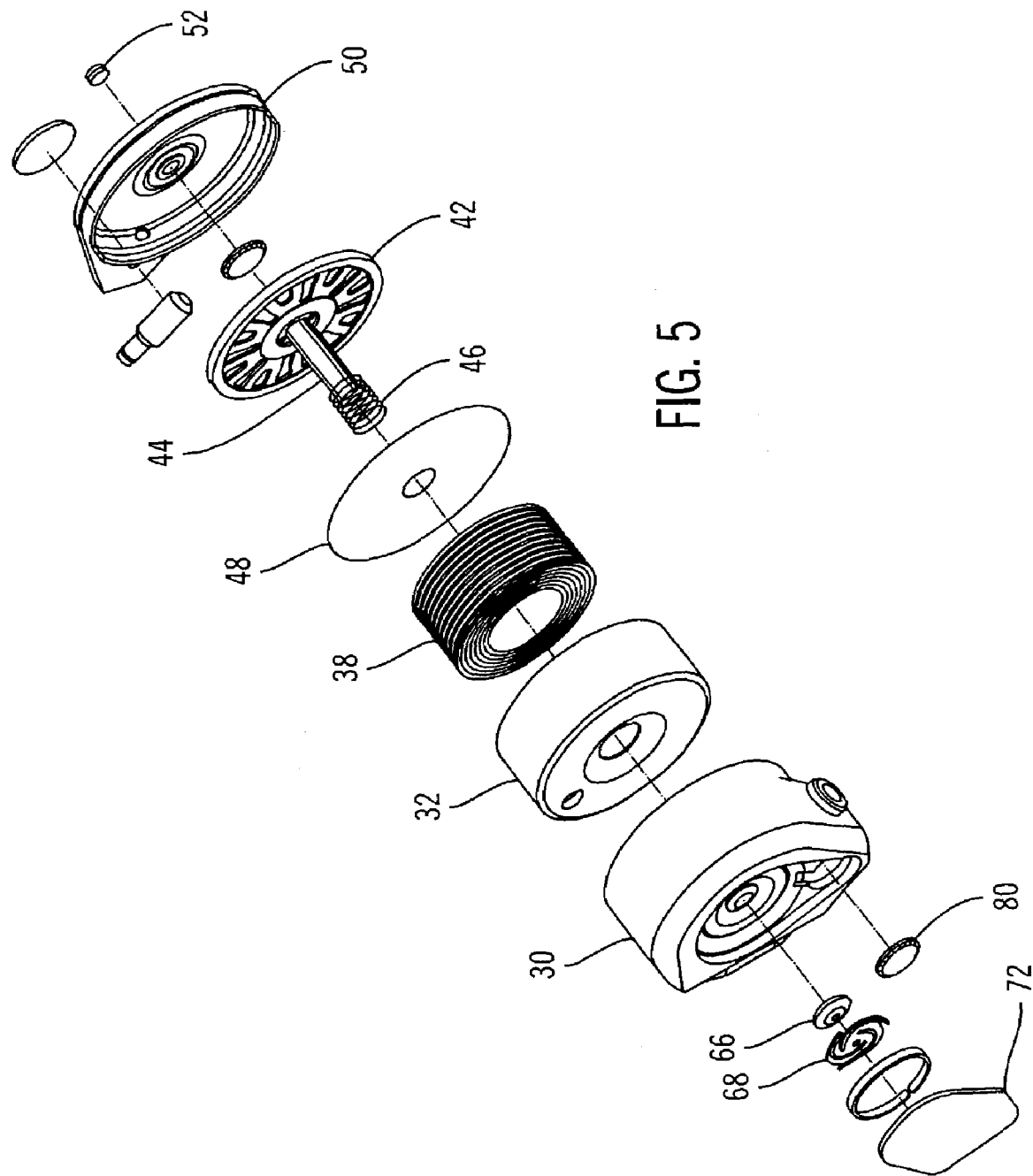
FIG. 5 is a an exploded view of an embodiment of the drive mechanism shown in FIGS. 3 and 4.

A drive mechanism as shown in FIGS. 3 and 4 may be constructed by providing components as shown in FIG. 5 and assembling the components in any suitable sequence. The components may be made according to any suitable process including, but not limited to molding, machining, extruding, sintering, casting, combinations thereof or the like.

The coil 38 may be inserted into the annular interior 33 of the coil cup 32, with the coil leads extended through a coil lead opening 84 in the coil cup. The coil may be impregnated or partially impregnated with a fill material of epoxy or the like, for adhering the coil to the coil cup and for sealing or partially sealing the coil. The fill material may also be used to adhere the barrier plate to the coil members, to avoid warping or bulging of the barrier plate after assembly.

The coil cup 32 and coil 38 maybe inserted into the interior 31 of the housing 30, with the coil leads (which may be wire leads or flexible conductive tabs) extending through a coil lead opening 86 in the housing 30. In preferred embodiments, the coil cup and housing are configured to provide a tight, friction fit therebetween, without requiring additional means of adhering the two components together. In other embodiments, the coil cup 32 and housing 30 may be coupled together by any suitable adhesive material or other adhering methods, including, but not limited to welding, brazing, of the like.

The barrier 48 may be placed over the coil, coil cup and housing sub-assembly. The barrier 48 may be adhered to the housing by one or more adhering points or continuously along the circumference of the barrier 48, with any suitable adhesive material or other adhering methods, including, but not limited to welding, brazing, soldering or the like. Alternatively, or in addition, the barrier 48 may be held in place by a shoulder portion of the cover 50, as shown in FIGS. 3 and 4. In addition, as noted above, the barrier 48 may be adhered to the coil 38 by fill material in the coil. In preferred embodiments, the barrier 48 is held in a generally flat relation relative to the coil cup and coil. To enhance this flat relation, the coil cup and housing may assembled together and then machined to planarize the barrier contact surfaces, prior to inserting the coil in the coil cup and prior to adding fill material to the coil.

Once the barrier 48 is placed over the coil, coil cup and housing, the actuator 40 may be added to the sub-assembly. First, however, the actuator spring 46 is placed around the piston portion 44, adjacent the armature portion 42 of the actuator. Then the free end of the piston portion 44 is passed through the axial channel 35 of the housing 30, with the armature end of the actuator arranged adjacent the barrier 48.

The cover member 50 may then be disposed over the armature end of the actuator and secured to the housing 30. In preferred embodiments, the cover member 50 is adhered to the housing by one or more adhering points or continuously along the circumference of the cover member 50, with one or more welds or any other suitable adhering methods, including, but not limited to adhesive materials, brazing or the like. The inlet filter 58 and inlet cover 62 may be pre-assembled with the cover member 50, prior to adding the cover member to the sub-assembly. Alternatively, the filter 58 and inlet cover 62 may be added to the cover member 50 after the cover member 50 is assembled onto the housing 30. In preferred embodiments, the filter 58 is disposed within the inlet chamber 56 and, then, the inlet cover 62 is adhered to the cover member 50 by one or more adhering points or continuously along the circumference of the inlet cover, with one or more welds or any other suitable adhering methods, including, but not limited to adhesive materials, brazing or the like.

The valve side of the drive mechanism may be assembled before or after the above-described components are assembled. On the valve side of the drive mechanism, the valve member 66 is disposed within the outlet chamber cavity 64 of the housing 30, adjacent the opening to the axial channel 35. The valve spring 68 is then disposed within the outlet chamber cavity 64, adjacent the valve member 66. The ring 70 is then disposed in the cavity 64, adjacent the spring 68. Any suitable number of accumulators may be placed within each of the accumulator cavities 78. The valve cover 72 may then be placed over the outlet chamber cavity 64 and accumulator cavities 78. In preferred embodiments, the housing 30 is provided with a recess 88 around the periphery of the cavities that form the outlet chamber cavity 64, accumulator cavities 78, outlet port 74 and flow passage 76, for providing a seat for the valve cover 72. In this manner, the valve cover 72 fits within the recess 88, flush with the housing 30. Also in preferred embodiments, the valve cover 72 is adhered to the housing 30 by one or more adhering points or continuously along the circumference of the valve cover, with one or more welds or any other suitable adhering methods, including, but not limited to adhesive materials, brazing or the like.

The volume of the piston chamber 65, the compression of the actuator spring 46 and the position of the actuator 40 in the retracted position shown in FIG. 3 may be adjusted by the adjusting the position of the adjusting plunger 52. In one preferred embodiment, the adjusting plunger includes a threaded cylindrical member, which engages corresponding threads in a plunger aperture in the cover member 50, to allow adjustment in a screw-threading manner. The diaphragm 59 under the plunger 52 contacts the armature portion 42 of the actuator, inside of the cover member 50. The other end of the plunger 52 may be provided with a tool-engagement depression, for allowing engagement by a tool, such as a screw-driver, Allen wrench or the like, from outside of the cover member 50. By engaging and rotating the plunger 52 with a suitable tool, the depth that the plunger extends into the cover member 50 may be adjusted, to adjust the retracted position of the armature portion 42 relative to the barrier 48 (to adjust the gaps between the pole sections 47, 49 of the armature and pole sections formed by the coil cup 32, when the actuator is in the retracted position of FIG. 3). In one preferred embodiment, adjustments of the plunger 52 are made during manufacture. In that embodiment, the adjusted position is determined and set by welding or otherwise adhering the plunger 52 in the adjusted position during manufacture. In other embodiments, the plunger 52 is not set and welded during manufacuture, to allow adjustment of plunger 52 after manufacture.

The resulting drive mechanism 20 may, therefore, be constructed to provide a relatively thin form factor and, yet provide a reliable operation that can deliver a relatively constant flow pressure and relatively precise volumes of infusion medium. A number of features can provide, or be combined to contribute to, reductions in the thickness form factor of the drive mechanism. For example, the coaxial arrangement of components such as the piston portion 44 and the coil 38, with a flow channel formed within the piston channel 35, can be implemented with a smaller thickness form factor (in the vertical dimension of FIGS. 3 and 4) than alternative arrangements in which those components are arranged adjacent each other in the thickness dimension.

Furthermore, the arrangement of an inlet volume 51 on one side of the coil 38 and an outlet chamber 64 on the opposite side of the coil 38, with a flow passage through the channel 35 in the coil 38 can also contribute to a reduction in the required thickness dimension of the drive mechanism, by allowing the coil 38 and channel 35 to share a common portion of the thickness dimension. The arrangement of the armature portion 42 to move within the inlet volume 51 allows those features to share a common portion of the thickness dimension. The arrangement of the outlet chamber 64 in a central location within the same housing that has the coil cup cavity allows those features to be formed in relatively close proximity to each other in the thickness dimension. The arrangement of the outlet chamber, outlet port and accumulator cavities in the housing 30 allows those features to share a common portion of the thickness dimension of the drive mechanism. Further features, including recessed shoulders 39 for the actuator spring 46, the use of a relatively flat valve spring 68 and general attention to minimizing thickness dimensions of components, where possible, can also contribute to reductions in the overall thickness dimension of the drive mechanism.

In addition, a number of features described herein can provide, or be combined to contribute to, the efficient use of power to, prolong the operational life of the drive mechanism. For example, a reduction in leakage of electromagnetic flux during coil energization, and, thus, a more efficient use of the flux generated by the coil, may be provided by configuring the width $W_1$ of the pole surface on the inner wall 90 of the cup member wider than the width $W_2$ of the pole surface on the outer wall 92 of the cup member. Similarly, more efficient conduction of electromagnetic flux may be provided by an actuator configured with a wider inner pole surface 49 than its outer pole surface 47. Also, more efficient conduction of electromagnetic flux may be provided by an actuator configured with radial sections 45 connecting the annular inner and outer pole surfaces 49 and 47.

Operation of First Drive Mechanism Embodiment

In operation, the drive mechanism 20 employs electromagnetic and mechanical forces to move between retracted (FIG. 3) and forward (FIG. 4) positions, to cause infusion medium to be drawn into and driven out of the mechanism in a controlled manner. In the retracted position, the spring 46 urges the actuator 40 toward its retracted position shown in FIG. 3. When the coil 38 is energized to overcome the spring force of spring 46, the actuator 40 moves to its forward stroke position shown in FIG. 4. The movement of the actuator between retracted and forward positions creates pressure differentials within the internal chambers and volumes of the drive mechanism 20 to draw medium into the inlet 27 and drive medium out the outlet 28.

More specifically, when the coil 38 is de-activated (not energized or not energized in a manner to overcome the spring force of spring 46), the actuator 40 is held in its retracted position (FIG. 3) under the force of the spring 46. When the coil is deactivated immediately following a forward stroke, the spring 46 moves the actuator 40 to the retracted position of FIG. 3, from the forward position shown in FIG. 4. The openings 41 and 43 in the armature portion 42 of the actuator 40 provide passages for medium to pass and, thus, reduce viscous drag on the actuator. As a result, the actuator 40 may move to its retracted position (FIG. 3) relatively quickly.

Figure 11:
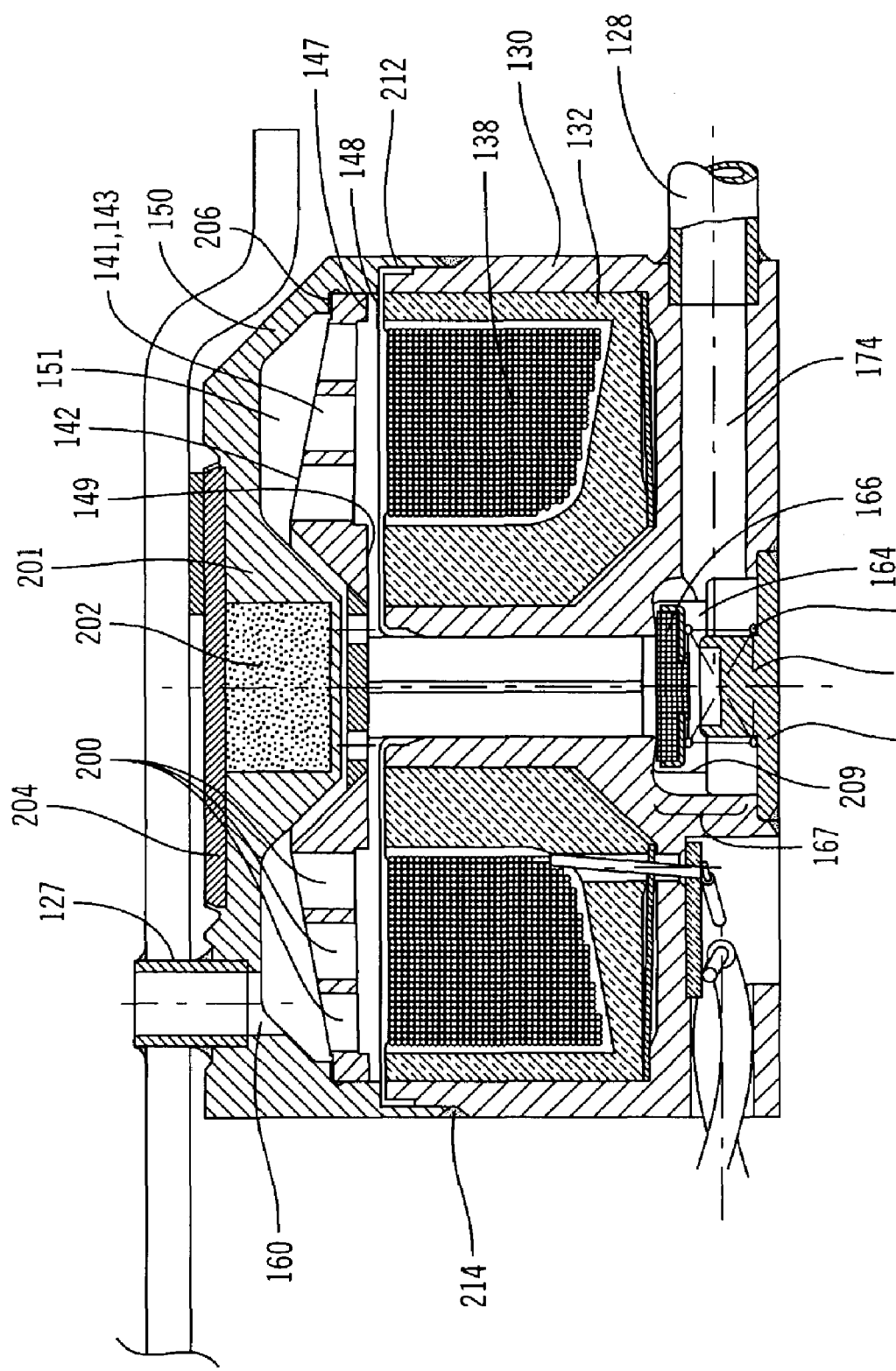
FIG. 11 is a cross-section view of another example embodiment of the drive mechanism of FIG. 2, in a retracted position or state.
Figure 12:
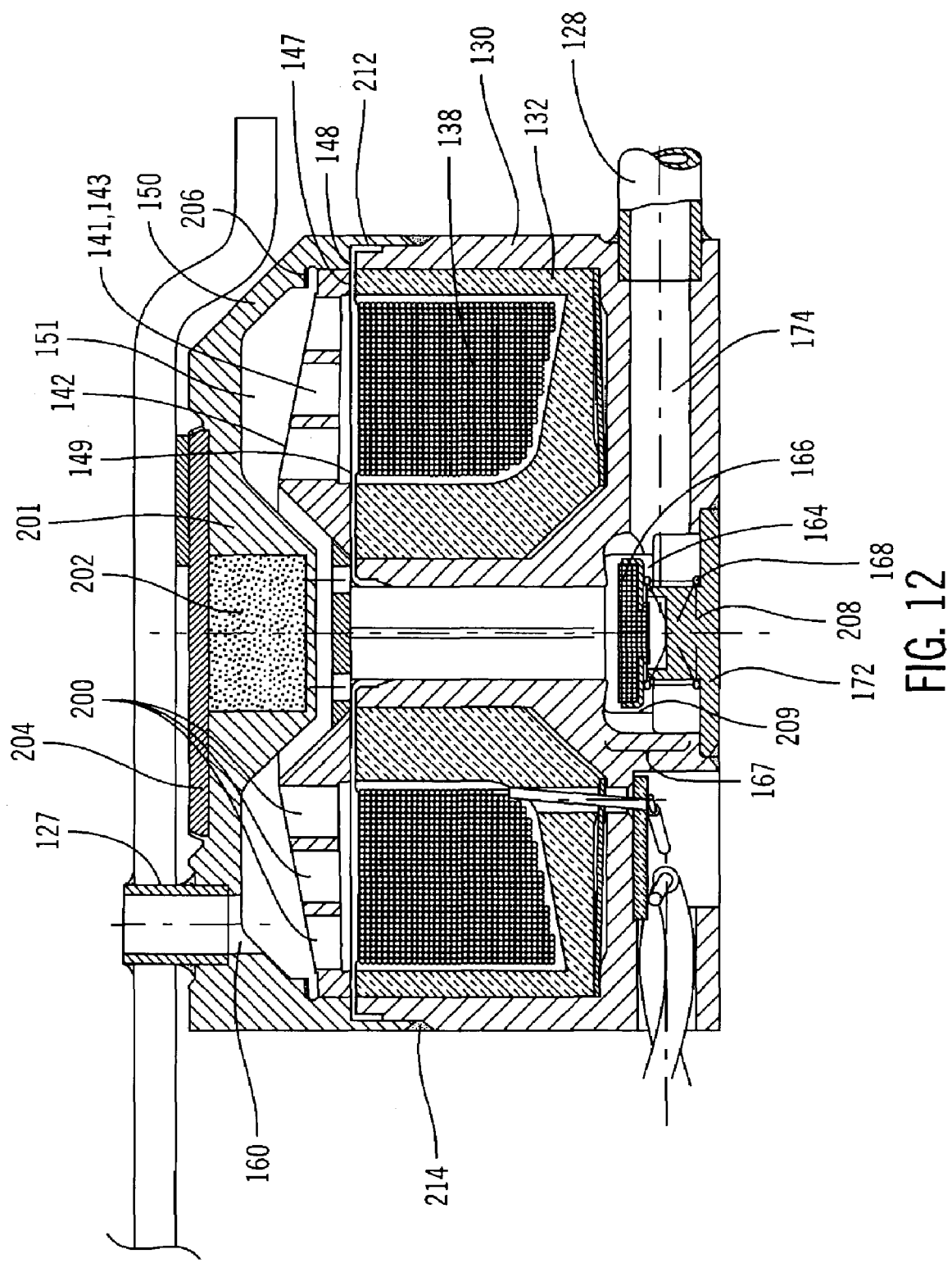
FIG. 12 is a cross-section view of the example drive mechanism embodiment of FIG. 11, in a forward stroke position or state.

As the actuator 40 retracts, the piston portion 44 of the actuator is retracted relative to the valve member 66, such that a piston chamber 65 volume is formed between the end of the piston portion 44 and the valve member 66. The formation of the piston chamber 65 volume creates a negative pressure which draws infusion medium from the volume 51 of the cover member 50, through the annular space between the piston portion 44 and the wall of the channel 35, and into the piston chamber 65. While not shown in FIG. 3, other embodiments (such as shown in FIGS. 11 and 12) may include one or more channels through the piston portion 44, to provide one or more additional flow paths to the piston chamber 65.

In the retracted position, a gap is formed between each of the annular pole surfaces 91 and 93 defined by the inner and outer walls 90 and 92 of the coil cup 32 and a respective annular surfaces of the inner and outer pole sections 49 and 47 of the actuator's armature portion 42. In particular, with reference to FIG. 3, a first gap 94 is formed between the annular pole surface 91 of the inner cup member wall 90 and the annular surface of the inner pole section 49. A second gap 95 is formed between the annular surface 93 of the outer cup member wall 92 and the annular surface of the outer pole section 47.

When the coil 38 is energized (or energized in a manner to overcome the spring force of spring 46), the actuator 40 is forced in the direction to close the gaps 94 and 95 and moves to its forward position (FIG. 4) under the influence of electromagnetic flux generated by the energized coil. In particular, the coil may be energized by passing an electrical current through the coil conductor to create electromagnetic flux. The electromagnetic flux defines a flux path through the coil cup walls, across the gaps 94 and 95 and through the armature portion of the actuator. The electromagnetic flux provides an attraction force between the annular surfaces 91, 93 of the coil cup 32 and the annular surfaces of the armature's pole sections 47, 49, to overcome the spring force of spring 46 and draw the armature 42 toward the coil cup.

As the armature portion 42 of the actuator is drawn toward the coil cup 32, the piston portion 44 of the actuator is moved axially through the channel 35, in the direction toward the outlet chamber 64. With the coil energized, the piston portion 44 continues to move under the action of the armature, until a mechanical stop is reached, for example, mechanical contact of the actuator 40 with the barrier 48, a portion of the housing 30 or cover member 50. In other embodiments, the motion may continue until the return force of the spring and fluid pressure overcomes the electromagnetic force provided by energizing the coil.

The movement of the piston portion 44 towards the stopping point reduces the volume of the piston chamber 65 and increases the pressure within the piston chamber until the pressure is sufficient to overcome the force of the valve spring 68. As the valve spring force is overcome by the pressure within the piston chamber, the valve member 66 is moved toward an open position, away from the opening between the piston chamber 65 outlet chamber 64. When the valve member 66 is in the open position, medium is discharged through the outlet chamber 64 and outlet 28 (FIG. 7).

When the coil is deactivated and the piston portion 44 is moved back to its retracted position, the pressure in the piston chamber 65 reduces and the valve member 66 is reseated under the action of the valve spring 68. This prevents fluid from flowing back into the drive mechanism, through the outlet. In addition, a negative pressure is created in the piston chamber 65 to draw medium into the chamber for the next forward stroke, as described above.

In this manner, energization of the coil 38 to move the actuator 40 to its forward position (FIG. 4) causes a measured volume of medium to be discharged from the outlet. As described above, when the coil 38 is de-energized, the actuator 40 is returned to the retracted position (FIG. 3) under the force of spring 46 and an additional volume of medium is drawn into the piston chamber 65 for the next discharging operation. Accordingly, the coil 38 may be energized and de-energized by a controlled electronic pulse signal, where each pulse may actuate the drive mechanism 20 to discharge a measured volume, or bolus, of medium. In preferred embodiments, the coil 38 may be electrically coupled to an electronic control circuit (not shown) to receive an electronic pulse signal from the control circuit for example, in response to a sensor signal, timer signal or other control signal input to the control circuit.

In preferred embodiments, when the piston motion is stopped at the end of the forward stroke, the valve-facing end of the piston portion 44 is in close proximity to the valve member 66, for example, spaced from the valve member 66 by no more than about ten percent (10%) of the piston diameter. In further embodiments, the valve facing end of the piston portion 44 is in contact with the valve member 66, at the end of the forward stroke. In this manner, gas that may be present in the infusion medium is less likely to accumulate within the piston chamber 65. More specifically, in some operational contexts, infusion medium may contain gas in the form of small bubbles that may migrate into the piston chamber 65 during filling of the piston chamber. As gas is significantly more compressible than liquid, too much gas within the piston chamber may adversely affect the ability of the drive mechanism to self prime.

In yet another embodiment the piston portion 44 may contact the valve member 66 at the end of the forward stroke and push the valve member 66 open. In this embodiment, it is less likely that gas will be trapped between the piston portion 44 and the valve member 66, and more likely that the chamber will be purged of gas.

The total ullage is the sum of (1) the volume at the valve-facing end of the piston portion 44 in a forward position (FIG. 4) and (2) the volume of the annular space between the piston portion 44 and the wall of the channel 35. In preferred embodiments, to provide self-priming properties, the total of those two volumes is selected to be about 25% of the volume of the volume 65.

When the actuator is stopped, for example, by contact with the barrier 48 or other mechanical stop structure, the coil current/voltage relationship changes. In preferred embodiments, control electronics (not shown) are connected to detect the change in coil current or voltage and deactivate the coil when the armature reaches the stop point. In this manner, the coil may be energized for only as long as the electromagnetic flux generated by the coil is providing useful work. Once the actuator motion is stopped and no further useful work is provided by the electromagnetic flux, the coil may be deactivated to reduce or minimize power consumption requirements of the drive mechanism.

In addition, such control electronics may also adapt to altitude changes and further reduce or minimize power consumption of the drive mechanism. In particular, a differential pressure exists between the inlet and the outlet ports of the drive mechanism during operation. The differential pressure resists the motion of the actuator in the forward direction and, consequently, consumes energy. However, the differential pressure tends to reduce with increasing altitude, requiring less energy to move the actuator. By deactivating the coil when the actuator stopping point is sensed, the drive mechanism can, effectively, automatically adjust to altitude changes and provide power consumption efficiency independent of altitude in which the drive mechanism is used. Conversley, the system may provide more power if there is a blocked catheter.

Further features described above may be employed for purposes of improving efficiency in power consumption, by more efficiently using the electromagnetic flux generated by the coil during energization. For example, in preferred embodiments, the width of the first gap 94 (in the dimension from the surface 91 to the surfaces of the inner pole section 49) is less than the width of the second gap 95 (in the dimension from the surface 93 to the surface of the outer pole section 47), when the actuator is in the retracted position. A greater outer pole spacing, relative to the inner pole spacing, can result in reduced residual flux that could otherwise cause the armature to stick in the forward position (the FIG. 4 position). In addition, a greater outer pole spacing reduces the squeezing effect on infusion medium within the second gap, as the armature 42 moves toward the forward position during actuation of the pump mechanism.

In further preferred embodiments, the width $W_1$ of the pole surface on the inner wall 90 is greater than the width $W_2$ of the pole surface on the outer wall 92 of the coil cup. In addition, the width $W_1$ of the inner pole surface 49 is greater than the width $W_2$ of the outer pole surface 47 of the armature, to correspond to the difference between the width of the inner wall 90 and the width of the outer wall 92 of the cup member. In one preferred embodiment, the width of the outer pole surface 47 of the armature is slightly larger than the width of the outer pole surface of the cup member wall 92 and the width of the inner pole surface 49 of the armature is slightly larger than the width of the inner pole surface of the cup member wall 90.

When the coil 38 is energized, the attraction force generated at the gap between a pair of pole surfaces is dependent upon the area of the pole surface. Forming the outer pole surfaces with a smaller width than the inner pole surfaces can compensate for the larger diameter and, thus, the larger surface area per unit of width of the outer pole surfaces relative to the inner pole surfaces. In preferred embodiments, the width of the pole surfaces are selected such that the attraction force at the inner pole is approximately 2.5 times the attraction force at the outer pole. This may be accomplished by configuring the width of the outer pole surface to have a surface area of approximately 2.5 times the surface area of the inner pole surface.

Second Drive Mechanism Embodiment and Operation

A drive mechanism 120 according to a further embodiment of the invention is shown, in cross-section, in FIGS. 11 and 12. In particular, FIG. 11 shows the drive mechanism 120 in a retracted position, while FIG. 12 shows the drive mechanism 120 in a forward position. Many aspects and features of the mechanism 120 are similar to corresponding aspects and features of drive mechanism 20 and for which reference is made to the above description of drive mechanism 20. Other aspects and features of drive mechanism 120 that differ from drive mechanism 20 are apparent from the drawings and the description below.

The drive mechanism 120 may be employed in the device 10 of FIG. 1, in a manner similar to that described above with respect to drive mechanism 20. Similar to the drive mechanism 20 of FIGS. 3 and 4, the drive mechanism 120 of FIGS. 11 and 12 includes an inlet 127, an outlet 128, a housing 130, a coil cup 132, an axial channel 135, a coil 138, an armature 142, a piston 144, a barrier member 148, a cover member 150 having an interior volume 151, a valve member 166, an inlet port 160, an outlet chamber 164, a piston chamber 165, a valve spring 168, a valve cover 172, and an outlet port 174. These features provide functions that correspond to the functions of the corresponding features of drive mechanism 20 of FIGS. 3 and 4 (shown in FIGS. 3 and 4 with corresponding reference numbers, without the hundredth digit). Insofar as these features have structural and operational similarities reference is made to the above descriptions of corresponding features, to avoid duplication of descriptions.

However, as noted above, various differences between the embodiments 20 and 120 are apparent from the drawings. One difference relates to the armature 142 and piston 144 which, together, form an actuator. In the embodiment of FIGS. 11 and 12, the armature and piston portions of the actuator are separate elements, while in the embodiment of FIGS. 3 and 4 described above, the piston and armature are portions of a single, unitary actuator structure.

In addition, the piston 144 has a central flow passage 145 extending between the two piston ends and open on each end to allow infusion medium to flow through the piston and, thus, through the channel 135. In the illustrated embodiment, a single flow passage 145 is provided along the central axis of the piston 144. In other embodiments one or more flow passages may be provided in a non-axial arrangement with or without an axial flow passage. With one or more central flow passages 145 through the piston 144 to allow passage of infusion medium through the channel 135, the spacing between the piston 144 and the wall of the channel 135 may be relatively small. As a result, the speed of refilling of the piston chamber may be increased.

The armature 142 has openings 141, 143 through which infusion medium may pass. While not shown in FIGS. 11 and 12, the openings 141, 143 may be arranged to provide radial flux conduction paths on the armature, as described above with respect to openings 41 and 43 in the armature 42 of FIGS. 3 and 4. In addition, the armature 142 may include further openings adjacent the central piston contact location.

The armature 142 has a tapered surface to define a generally frusto-conical shape having a thin cross-section at its outer periphery or outer pole 147, relative to the cross-section at the inner pole 149. The tapered surface of the armature 142 has a central indentation, in which an extended central portion 201 of the cover member 150 extends. A permanent magnet 202 is disposed within the central portion of the cover member 150 and a magnet cover 204 is attached to the cover member 150, over the magnet 202.

The armature 142 and piston 144 are drawn toward the retracted position shown in FIG. 3, by the attraction force of the permanent magnet 202. As a result, a spring (such as spring 46 in the embodiment of FIGS. 3 and 4) is not needed. However, further embodiments may employ various combinations of one or more permanent magnets and springs for urging the armature 142 and piston 144 toward the retracted position. In the retracted position, the armature 142 abuts a shoulder 206 on the cover member 150. In further embodiments, instead of abutting shoulders 206, the armature 142 abuts the extended central portion 201 of the cover member 150.

Figure 13:
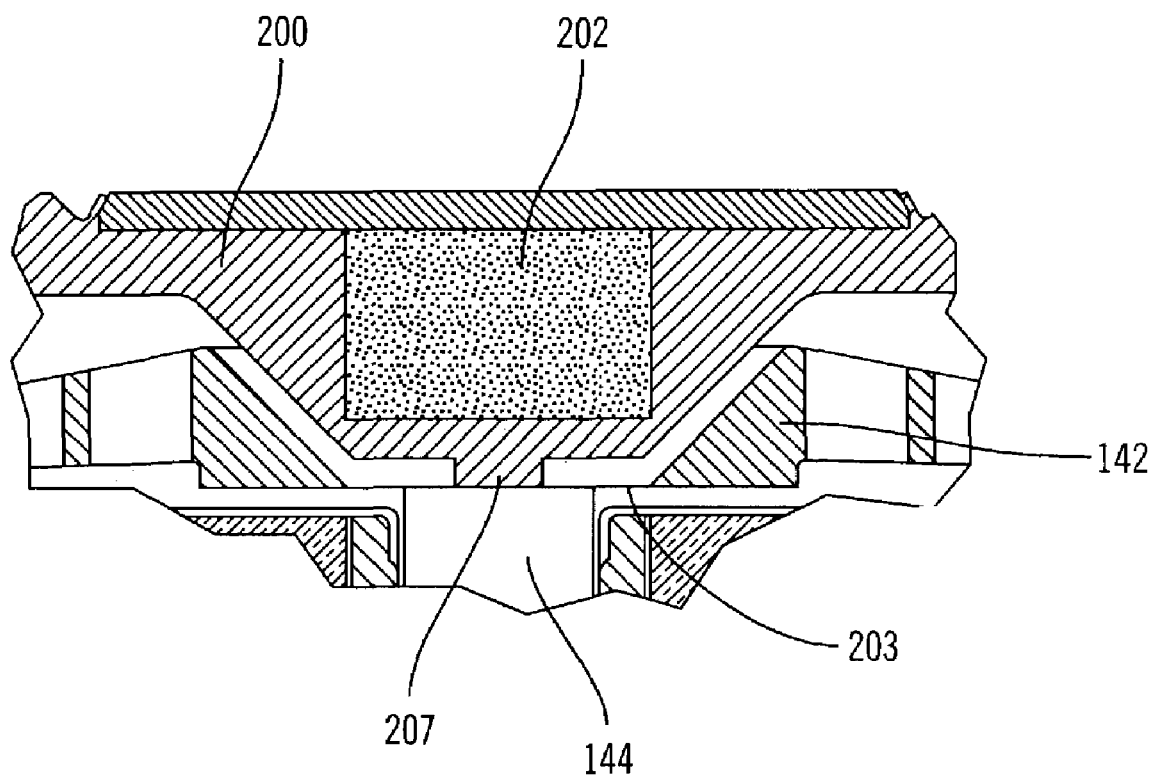
FIG. 13 is a partial cross-section view of a portion of the drive mechanism cover, armature and piston, according to a further embodiment of the invention.

In embodiments employing a magnet 202, the armature 142 may be configured with a central section 203 formed of a non-magnetic material, such as stainless steel, biocompatible plastic, ceramic, glass or the like, to allow the magnetic flux from the magnet 202 to have a greater attraction action on the piston 144. The portion of the armature 142 outward of the central section 203 is preferably made of a magnetically permeable material, as described above with respect to armature 42. In further embodiments, the central section 203 of the armature may be open. In such embodiments, the central extended portion 201 may include a further extension, shown at 207 in FIG. 13, to provide a stop for the piston 144 in its retracted or retracted position.

In yet further embodiments, an adjusting plunger, such as plunger 52 described above with respect to the embodiment of FIGS. 3 and 4, may be disposed through the cover member 150 to provide an adjustable stop for the armature 142 in the retracted position. For example, an adjustment plunger may extend through an aperture (not shown) formed in the magnet 202 or formed elsewhere in the cover member 150, to abut the armature in its retracted position.

In the embodiment of FIGS. 11 and 12, the inlet 127 and inlet port 160 extend vertically with respect to the orientation shown in those figures. However, other embodiments may employ a horizontal inlet port arrangement with respect to the orientation of the figures, such as shown in FIGS. 3 and 4. Likewise, embodiments as shown in FIGS. 3 and 4 may be implemented with a vertical inlet port arrangement as shown in FIGS. 11 and 12. Of course, other suitable inlet port arrangements may be employed without detracting from further aspects of the drive mechanism described herein.

The outlet chamber 164 in FIGS. 11 and 12 contains a valve assembly 167 comprising a valve member 166 and a valve spring 168. The spring 168 is a coil spring, rather than the flat, spiral spring 68 of FIGS. 3 and 4. The coil spring 168 is disposed around a central extended portion 208 of the valve cover 172 and, in the retracted position (FIG. 11), extends beyond the central extended portion 208 to support the valve member 166 in a spaced relation with respect to the central extended portion 208. In the forward position (FIG. 12), the valve member 166 compresses the coil spring and abuts against the central extended portion 208 of the valve cover 172. The interior walls of the outlet chamber 164 are provided with ribs or flutes 209 to help guide the valve member 166 between open and closed positions (shown in FIGS. 11 and 12, respectively).

While a coil spring arrangement is shown in FIGS. 11 and 12 and a flat spring arrangement is shown in FIGS. 3 and 4, either a coil or flat spring arrangement may be employed in either of those embodiments. A flat spring arrangement may provide a thinner form factor and adjustment capabilities by selecting or adjusting the thickness of the ring 70, as described above. However, a coil spring arrangement may provide a more stable support for embodiments in which the piston portion of the actuator is separable from the armature portion.

The barrier member 148 in FIGS. 11 and 12 may have folded inner and outer edges 210 and 212, which fold over the inner and outer walls of the housing 130. The inner and outer housing walls are formed with annular indentations for receiving the folded edges 210 and 212 of the barrier member 148. The folded edges of the barrier member enhance the sealing capabilities of the barrier member. In addition, the folded edges allow the barrier member to be welded, or otherwise adhered, to the housing 130 along a surface 214 on the lateral side of the housing's outer wall. The folded edges allow the barrier to be machined (for example, lapped) flat, after welding. While a folded edge barrier member arrangement is shown in FIGS. 11 and 12 and a flat barrier member arrangement is shown in FIGS. 3 and 4, either a folded edge or flat arrangement may be employed in either of those embodiments.

The drive mechanism 120 operates similar to the drive mechanism 20 described above. However, unlike-the armature 42 and piston 44 in the drive mechanism 20, the armature 142 and the piston 144 of the drive mechanism 120 are capable of moving independently and infusion medium is allowed to flow through the passage 145 in the piston when the piston is physically separated from the armature.

Similar to the embodiment described above, the drive mechanism 120 employs electromagnetic and mechanical forces to move between retracted (FIG. 11) and forward (FIG. 12) positions, to cause infusion medium to be drawn into and driven out of the mechanism in a controlled manner. In the retracted position, the magnet 202 urges both the armature 142 and the piston 144 toward their retracted positions shown in FIG. 11. In this position, a central portion 203 of the armature 142 contacts the piston 144 and blocks one end of the passage 145 in the piston 144. In this manner, when the piston 144 and armature 142 are in retracted positions, the armature 142 blocks the flow of fluid through the passage 145 in the piston 144 and, thus, inhibits back flow of fluid from the outlet chamber side of the piston.

When the coil 138 is energized, the armature 142 is attracted to the coil cup 138 by electromagnetic flux as described above. The attraction force is sufficient to overcome the force of magnet 202 and cause the armature to move and close the gap in the electromagnetic flux path between the armature 142 and the coil cup 132. As the piston 144 is in contact with the armature 142, the piston also moves, reducing the volume of the piston chamber 165. During movement of the armature and piston toward their forward positions, the central portion 203 of the armature 142 remains in contact with the piston 144 and continues to block the passage 145 and inhibit back flow of fluid from the piston chamber 165. As the piston 144 moves toward its forward position, the pressure in the piston chamber 165 increases until it is sufficient to overcome the force of the spring 168 and move the valve member 166 to the open position. When the valve member is opened, infusion medium within the piston chamber 165, passage 145 and within the volume between the piston 144 and the wall of the channel 135 is discharged into the outlet chamber and through the outlet port 174.

The piston 144 continues to move under the force of the armature 142 until the armature 142 contacts the barrier 148 or a mating face (not shown) of the housing 130 or cover 150. When the armature stops, the piston 144 is in preferably in close proximity or contact with the valve member 166, to inhibit migration of bubbles into the piston chamber as described above and, thereby, improve self priming capabilities. Also for improving self priming capabilities, it is preferred that the total ullage, determined as the sum of the volume of the passage 145 through the piston and the volume between the piston and the valve member when the piston is in the forward stroke position (FIG. 12), be about 25% of the volume of the piston chamber 165 in the retracted or retracted position (FIG. 11). As described above, a mechanically actuated check valve may be provided in the valve member 166 or in the passage 145 of the piston, to vent gas from the piston chamber 165 and, thus, further improve the self priming capabilities of the drive mechanism.

When the coil 138 is de-energized, the ferro-magnetic armature 142 and piston 144 attracted by the magnet 202, to move from the forward stroke position of FIG. 11, toward the retracted or retracted position of FIG. 12. However, due to viscous drag caused by the close proximity of the outer surface of the piston 144 and the surface of the channel 135 wall, the piston returns to the retracted position at a slower rate than the armature 142. As a result, the armature 142 separates from the piston 144 and opens the passage 145 in the piston to the infusion medium present in the interior 151 of the cover member 150. In this manner, during the return stroke, infusion medium from the cover interior 151 is drawn into the passage 145 through the piston 144 and into the piston chamber 165.

As the piston 144 moves to the retracted position, the pressure within the piston chamber 165 reduces to help draw medium into the piston chamber and to allow the valve member 166 to close. After the piston 144 completes its return stroke, it is again in contact with the armature 142 and the passage 145 in the piston is again blocked by the armature 142. The piston is then ready for its next forward stroke.

Further Embodiments

Figure 14:
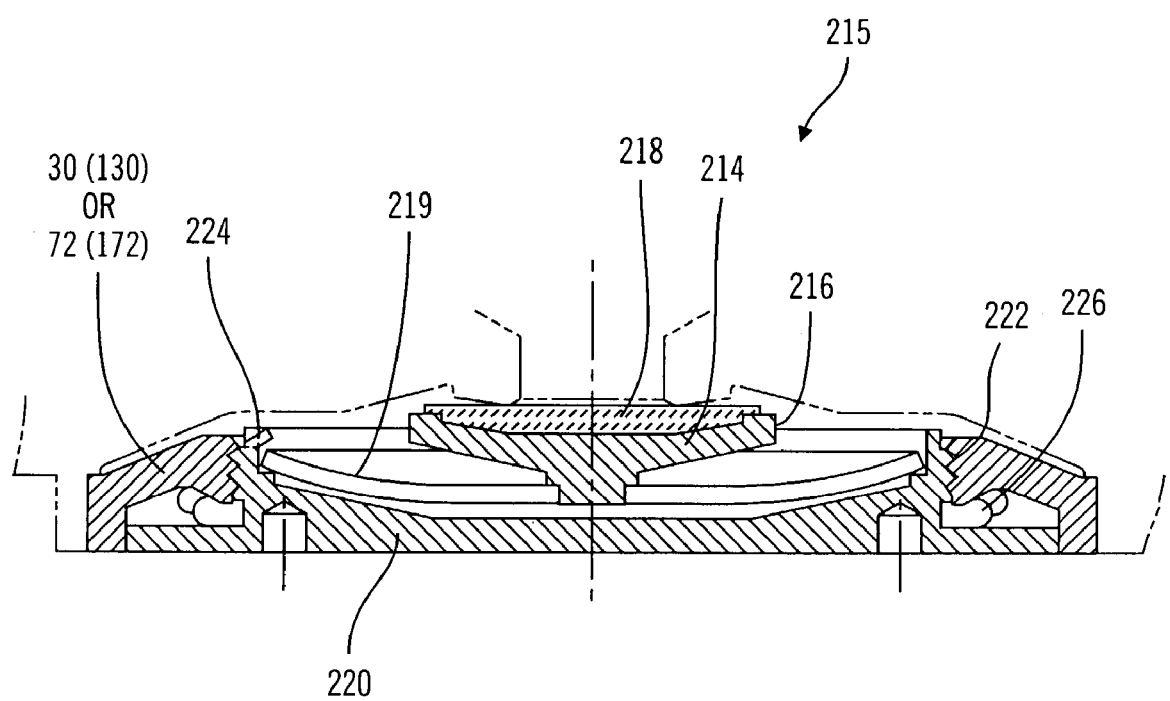
FIG. 14 is a cross-section view of a valve assembly structure according to a further embodiment of the invention.

While embodiments described above may include valve assemblies 67 and 167, as shown in the FIGS. 3, 4, 11 and 12, other embodiments may employ other suitable valve assembly structures. For example, in a further embodiment, the valve assembly structure may be assembled separately from the rest of the drive mechanism and, then, connected, as a unitary structure, to the drive mechanism housing. A representive example of a pre-assembled, unitary valve assembly structure 215 is shown in FIG. 14, where the valve assembly 215 includes a valve member 216 having a rigid portion 217 and a resilient portion 218, similar to the valve member 66 described above. The valve assembly 215 also includes a valve spring 219 similar to the valve spring 68 described above. The valve assembly 215 further includes a threaded valve cap 220 in which the spring 219 and the valve member 216 are disposed. The valve spring 219 supports the valve member 216 for movement within the valve cap 220. The valve assembly, including the threaded valve cap 220, the spring 219 and the valve member 216 may be assembled together to form a unitary structure, for example, during or prior to the assembly of the rest of the drive mechanism.

Figure 15:
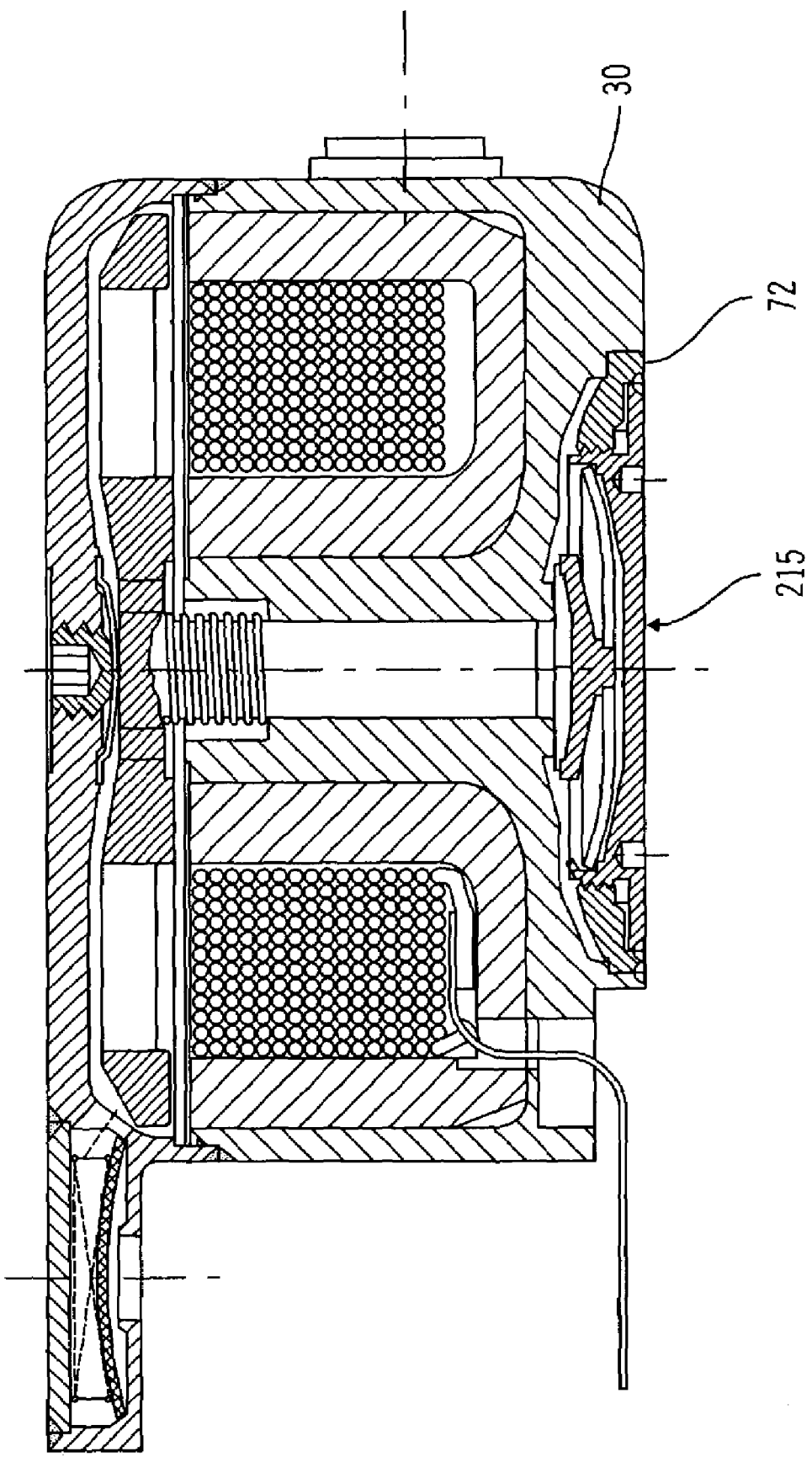
FIG. 15 is a cross-section view of a drive mechanism having a valve assembly structure in accordance with the embodiment of FIG. 14.

The valve cap 220 may be composed of any suitable biocompatible and infusion medium compatible material, including, but not limited to stainless steel, titanium, biocompatible plastic, ceramic, glass or the like, and includes a threaded outer peripheral surface 222, which is configured to engage a correspondingly threaded inner peripheral surface 224 of an aperture formed in the drive device housing 30 (or 130). Alternatively, the threaded aperture may be formed in a valve cover (72 or 172 shown in FIGS. 3 and 11). Thus, once the valve assembly 215 is assembled into a unitary structure, the unitary valve assembly may be coupled to the rest of the rest of the drive mechanism, by threading the valve assembly into the threaded aperture of the drive mechanism housing or valve cover, as shown in FIG. 15. In alternative embodiments, the valve assembly may be coupled to the housing or valve cover by other suitable coupling methods, including, but not limited to, adhesives, welds, brazing or the like. An O-ring seal or other suitable sealing material 226 may be disposed between the valve cap 220 and the housing (or valve cover) to help seal the aperture.

Figure 16:
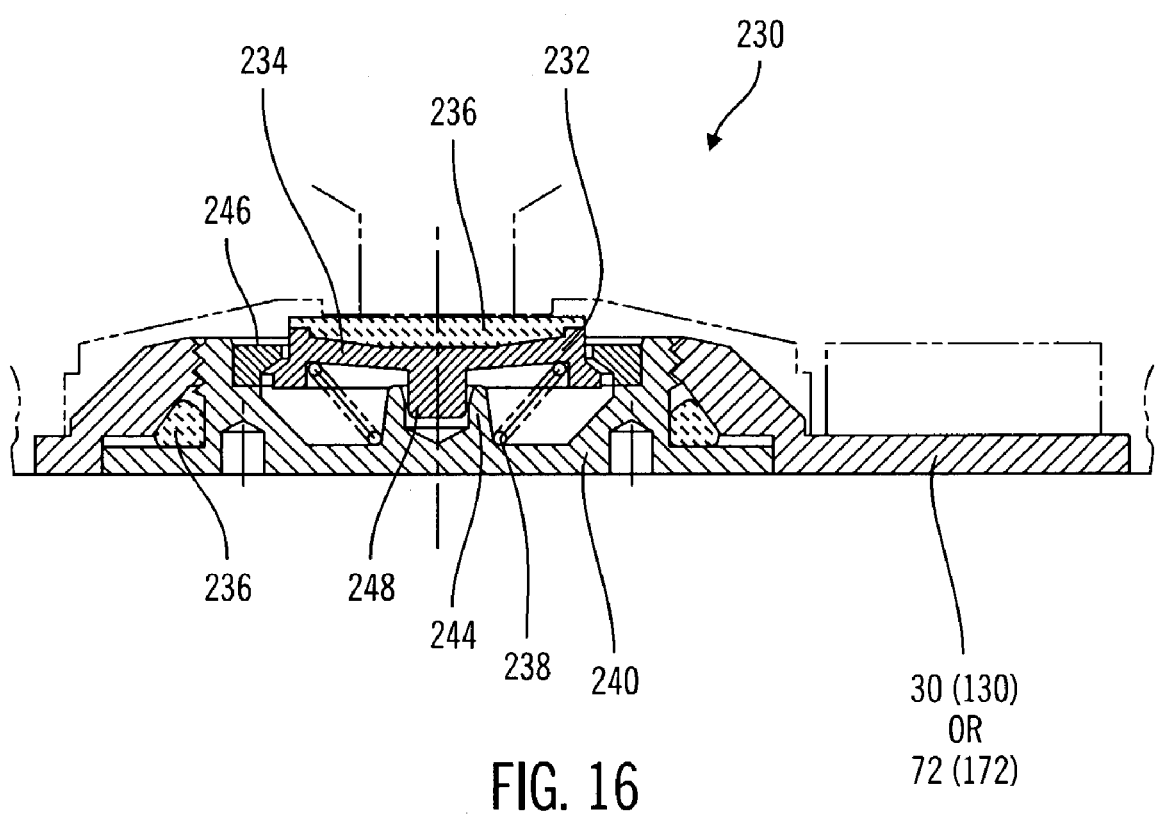
FIG. 16 is a cross-section view of a valve assembly structure according to yet a further embodiment of the invention.

Another embodiment of a valve assembly structure 230 is shown in FIG. 16, where the valve assembly 230 includes a valve member 232 having a rigid portion 234 and a resilient portion 236. The valve assembly 230 also includes a valve spring 238. The valve assembly 230 further includes a valve cap 240 in which the spring 238 and the valve member 232 are disposed. The spring 238 supports the valve member 232 for movement within the valve cap 240. The valve assembly, including the valve cap 240, the spring 238 and the valve member 236 may be assembled together to form a unitary structure, for example, during or prior to the assembly of the rest of the drive mechanism. Thus, as discussed above with respect to valve assembly 210, once the valve assembly 230 is assembled into a unitary structure, the unitary valve structure assembly may be coupled to the rest of the rest of the drive mechanism, by threading (or otherwise connecting) the valve cap 240 into an aperture in the drive mechanism housing 30 (or 130) or valve cover 72 (or 172). An O-ring seal or other suitable sealing material 236 may be disposed between the valve cap 240 and the housing (or valve cover) to help seal the aperture.

The valve member 232 in the valve assembly 230 includes a stem portion 242 which resides within a cylindrical guide 244 in the valve cap 240. The spring 238 abuts the outer peripheral surface of the guide 244. In this manner, the guide 244 helps maintain proper alignment of the valve assembly components during manufacture and over the operational life of the valve assembly. In addition, the valve assembly 230 includes an annular retainer member 246, which may be composed of any suitable biocompatible and infusion medium compatible material, including, but not limited to stainless steel, titanium, biocompatible plastic, ceramic, glass or the like. The annular retainer member 246 provides a stop surface for abutting a lip 248 of the valve member 232.

Unitary valve assembly structures, such as valve assemblies 215, 230 or the like, may be assembled separately from the other components of the drive mechanism and may be connected, as a pre-assembled structure, to the housing or valve cover of the drive mechanism during the process of assembling the drive mechanism. In this manner, unitary valve assembly structures, such as valve assemblies 215, 230 or the like, may be pre-assembled in bulk to reduce manufacturing costs. Furthermore, such unitary valve assembly structures may be assembled and tested prior to connection to other components of the drive mechanism, for example, in testing environments having controlled properties, such as controlled valve seat dimensions, valve seat pressures, and the like. Moreover, unitary valve assembly structures, such as valve assemblies 215, 230 or the like, may be coupled to the housing or valve cover of a drive mechanism in an adjustable manner, to adjust the seating force of the valve member against its valve seat (the valve seat end of the piston channel of the drive mechanism). In the above-described embodiments, the valve seat force may be adjusted by threading the valve cap further into or further out of the threaded aperture in the housing or valve cover. Other embodiments may employ other suitable adjustment methods, including, but not limited to, a friction fit between the valve cap and the housing or valve cover.

As described above, valve members 66, 158, 212 and 232 may include an elastomeric, compliant portion for abutting the valve seat and a rigid portion for supporting the compliant portion. Compliant valve materials can improve sealing capabilities and/or operate with low sealing forces. However, in environments in which it is desirable for each pump stroke to dispense an accurate volume of medium, the compliant portion of the valve member may introduce errors in the output volume accuracy. The amount of deflection of the compliant sealing member may significantly affect several aspects of the system, including, but not limited to, fluid refill into the piston chamber, amount of ullage or usable volume, interference of the compliant member with the piston, and change the effective volume of the piston chamber over time.

Therefore, valve members according to further embodiments of the invention as described with reference to FIGS. 17–22 are configured to provide the benefits of a compliant valve member, yet reduce or eliminate the above-noted adverse effects on output volume accuracy. In the embodiment shown in FIG. 17, a valve member 250 is supported for movement between an open and closed position by a valve spring 251, for example, in a manner similar to that described above with respect to valve members 66, 158, 212 and 232 and valve springs 68, 168, 218 and 238. The valve member 250 includes a compliant portion 252 supported by a rigid portion or retainer 254. The compliant portion 252 may be composed of a suitably compliant material such as, but not limited to, an elastomer. The retainer 254 may be composed of a suitably rigid, biocompatible and infusion medium compatible material, such as, but not limited to, titanium, stainless steel, biocompatible plastic, ceramic, glass, gold, platinum or the like.

Figure 17:
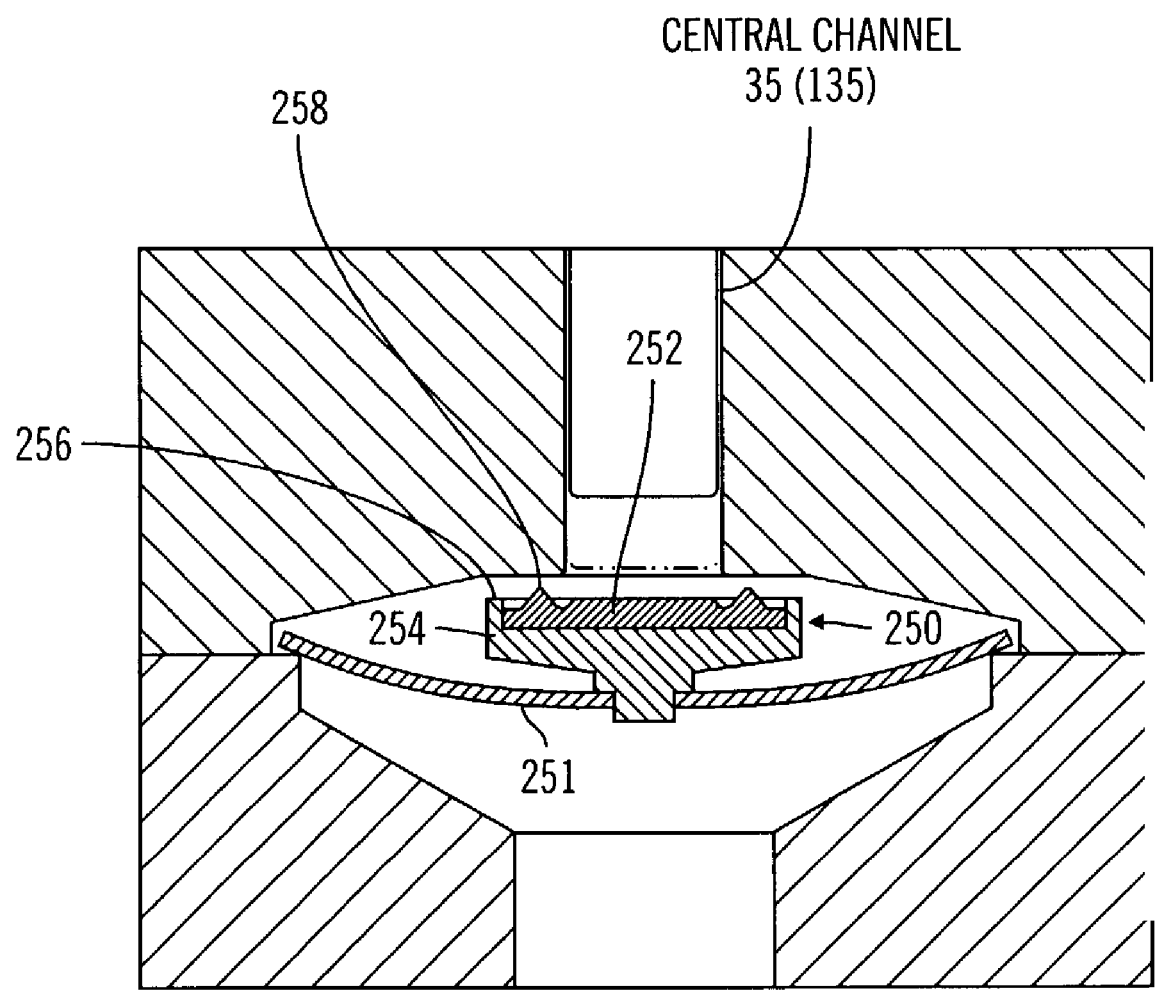
FIG. 17 is a cross-section view of a valve assembly structure according to yet a further embodiment of the invention.

The compliant portion 252 in FIG. 17 protrudes a set distance from an extended face of the retainer 254, such that the force of the compliant portion 252 against the valve seat provided by the spring 251 and any head pressure (back pressure from the outlet) is sufficient to seal the valve member 250 against the valve seat. The valve member 250 includes one or more stop surfaces, which may be formed, for example, as one or more projecting portions of the retainer 254. In the FIG. 17 embodiment, a stop surface 256 comprises the end of an annular wall that extends around the circumference of the compliant portion 252. Thus, in the FIG. 17 embodiment, the retainer 254, with its annular wall 256, forms a cup for containing the compliant portion 252. The stop surface on the end of the annular wall is located at a position relative to the protruding position of the compliant portion such that the force of compliant portion 252 against the valve seat (by spring 251 and any head pressure) is sufficient to compress the protruding compliant portion enough to allow the stop surface 256 to engage the valve seat. The compliant portion 252 may include one or more annular projections 258 surrounding the end of the piston channel of the drive mechanism, to improve sealing capabilities of the valve member.

The stop surface 256, thus, provides a hard stop at a pre-defined position, defined by the position of the stop surfaces. By extending or configuring the protruding end of the compliant portion 254, the compliant portion 254 may form a seal against the valve seat or a surface adjacent the valve seat, at least by the time the stop surface 256 makes hard contact with the valve seat or a surface adjacent the valve seat. Once a seal is formed (between the compliant portion 254 and the valve seat) and the stop surface 256 of the retainer 254 contacts the valve seat, further compression of the compliant portion and further variances in the piston chamber volume are arrested. As a result, the valve configuration may provide a pre-determined, accurate and repeatable piston chamber volume with each valve closure.

Figure 18:
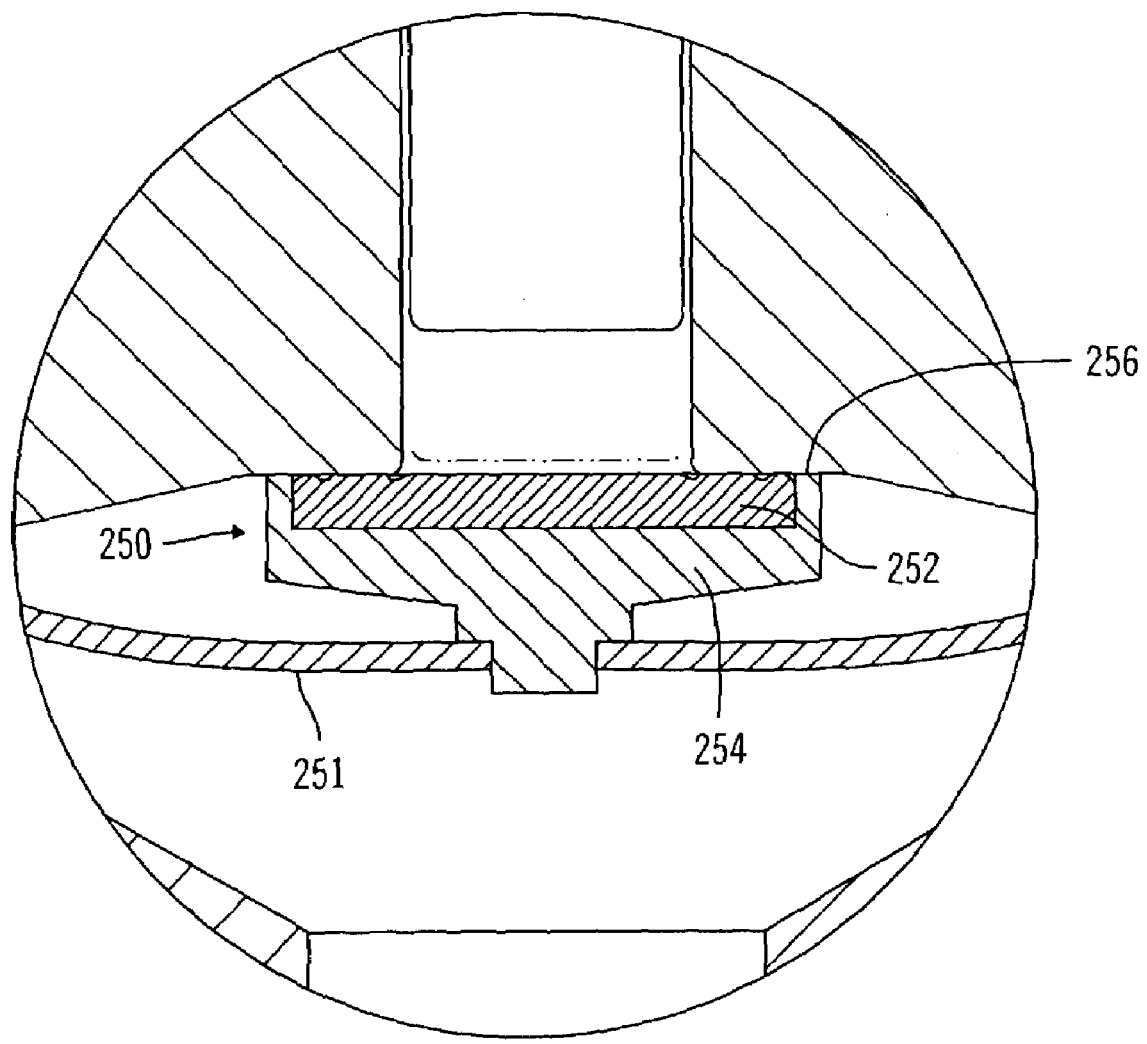
FIG. 18 is a cross-section view of a valve assembly structure according to yet a further embodiment of the invention.
Figure 19:
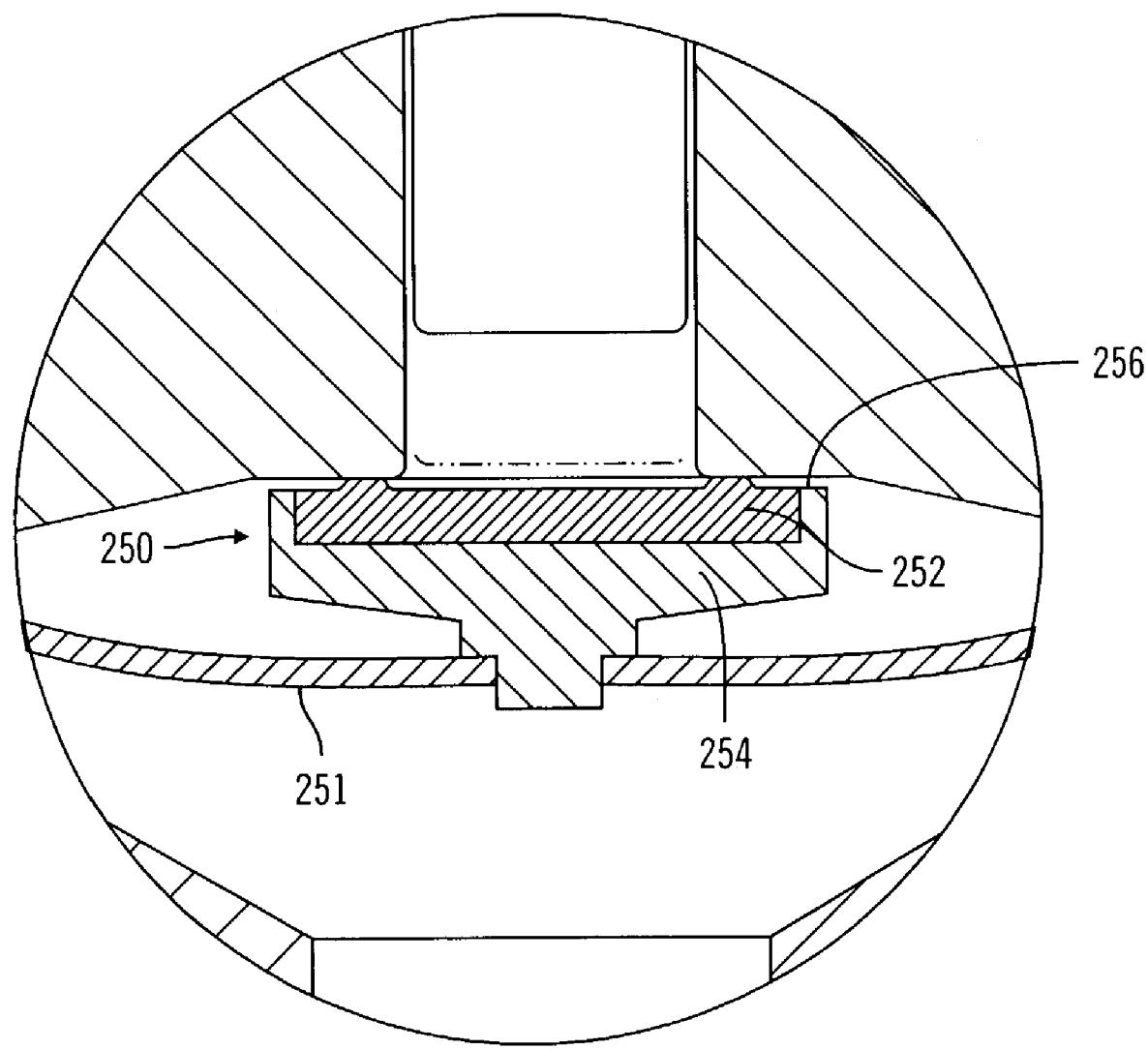
FIG. 19 is a cross-section view of a valve assembly structure according to yet a further embodiment of the invention.

In preferred embodiments, the compliant portion 252 forms a seal against the valve seat upon the retainer 254 making contact with the valve seat or a surface adjacent the valve seat, as shown in FIG. 18. Alternatively, a seal may be formed prior to the retainer 254 making contact with the valve seat or a surface adjacent the valve seat, as the protruding end of the compliant portion 252 compresses against the valve seat, as shown in FIG. 19. For example, design optimization, including but not limited to, minimizing load associated with the valve or energy used by the system, may utilize a valve return spring with less force. For that operating condition, the spring may be designed or selected in conjunction with the compliant portion such that the load supplied by the spring does not fully compress the compliant material. Under certain conditions, a head pressure may be generated on the outlet side of the valve, forcing the valve retainer 254 to move axially an appropriate distance to achieve a hard stop of the stop surface 256 against the valve seat or a surface adjacent the valve seat.

Figure 20:
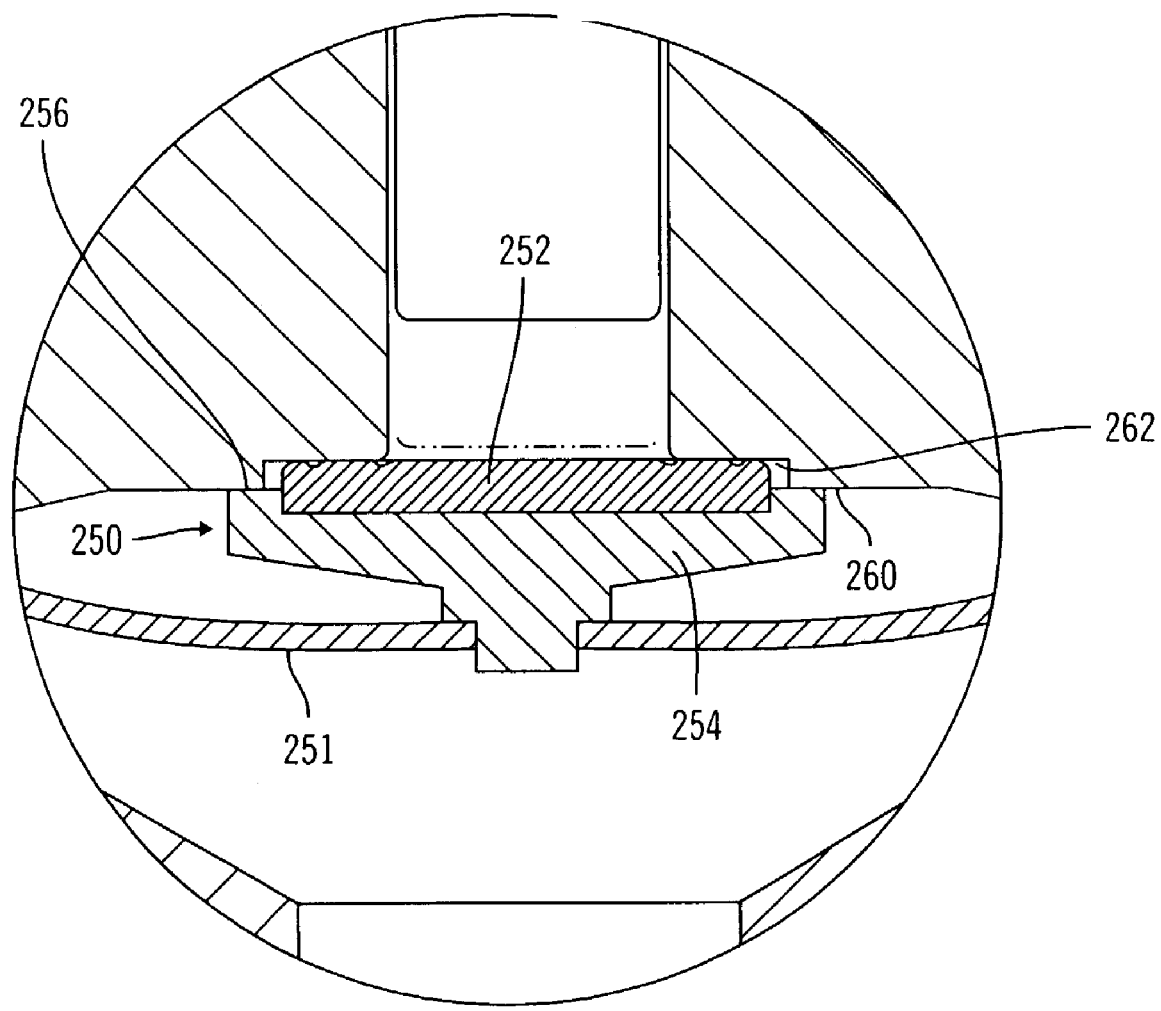
FIG. 20 is a cross-section view of a valve assembly structure according to yet a further embodiment of the invention.
Figure 21:
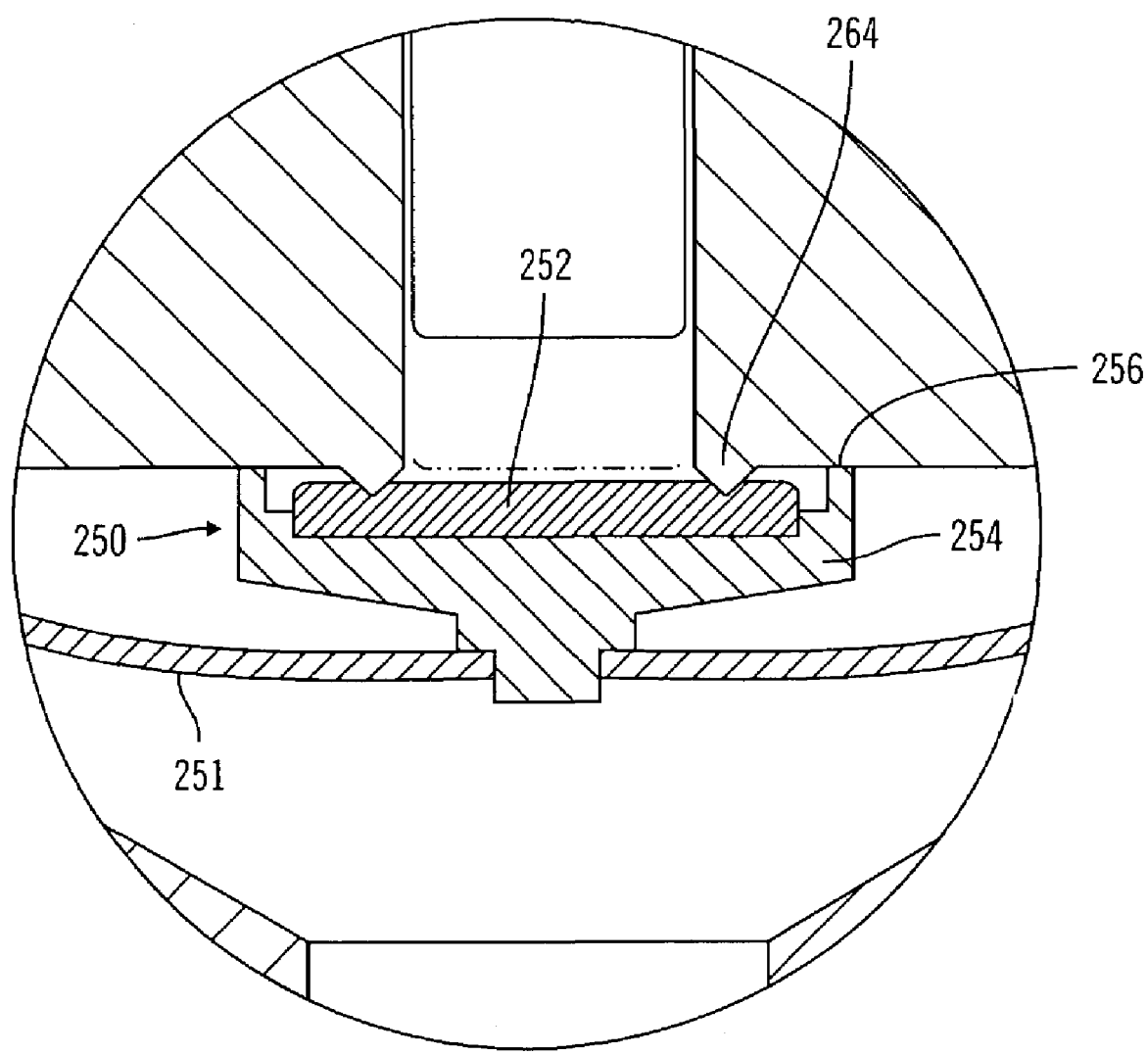
FIG. 21 is a cross-section view of a valve assembly structure according to yet a further embodiment of the invention.

In further valve configuration embodiments as shown in FIG. 20, the valve seat includes a projecting surface 260 and a recessed surface 262. The recessed surface 262 is positioned to contact the compliant portion 252 of the valve member 250 either at the same time as or prior to the projecting surface 260 making contact with the stop surface 256 of the retainer 254. In yet further valve configuration embodiments as shown in FIG. 21, the valve seat includes one or more annular projections 264 (one shown in FIG. 21), for engaging, and preferably compressing, the compliant portion 252 around the piston channel of the drive mechanism. The retainer 254 may include a stop surface 256 extended beyond the compliant portion 252, preferably a distance that is not so great as to inhibit the projection 264 from contacting or contacting and compressing the compliant portion 252 (for example, a distance less than the distance that the projection 264 projects beyond the valve seat surface that makes contact with the stop surface 256).

Figure 22:
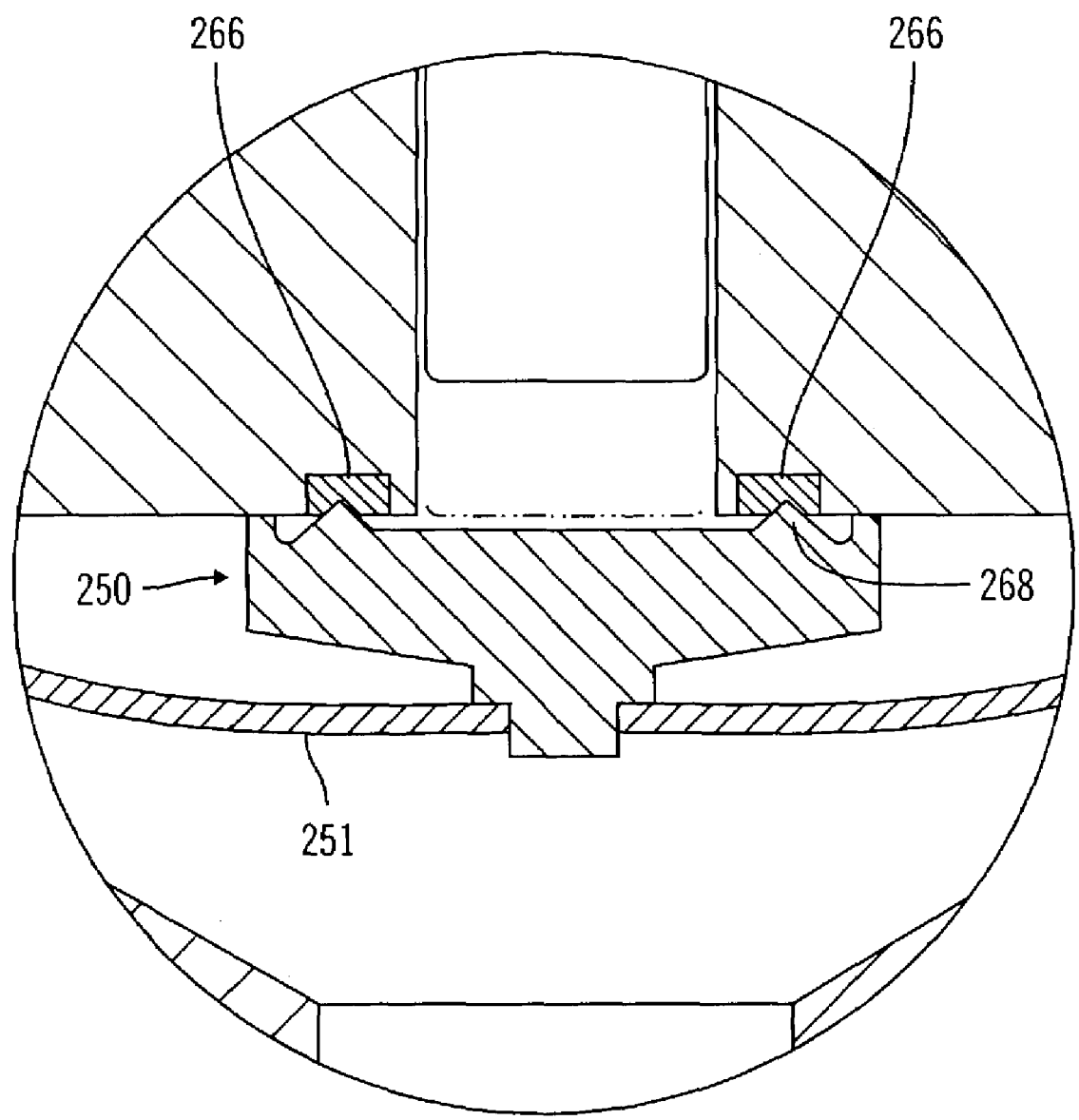
FIG. 22 is a cross-section view of a valve assembly structure according to yet a further embodiment of the invention.

In yet a further valve configuration embodiment as shown in FIG. 22, at least one annular compliant member 266 is disposed in the valve seat, surrounding the valve end of the piston channel of the drive mechanism. The compliant member 266 may be molded, press fit or otherwise fixed in place, for example, in an annular groove in the valve seat, surrounding the valve end of the piston channel. In the FIG. 22 embodiment, the valve member 250 need not include a compliant portion. Instead, in preferred embodiments, the valve member 250 includes at least one annular projection 268 arranged to engage the compliant member(s) 266. The valve member 250 may also include at least one stop surface 256 for contacting the valve seat and inhibiting further movement of the valve member in the direction toward the valve seat or a surface adjacent the valve seat. The stop surface 256 may make contact with the valve seat or a surface adjacent the valve seat upon the projection(s) 268 making contact with the compliant member(s) 266 and, more preferably, after the projection(s) at least partially compresses the compliant member(s) 266.

While drive mechanism embodiments described above employ a coaxial arrangement of the coil, piston channel and piston, other embodiments may employ a piston and piston channel located between, but not coaxial with, a plurality of spaced coils. For example three coils may be located in a spaced relation at three respective corners of a triangle, with the piston channel and piston located in the center of the triangle (surrounded by the three locations of the coils), and with the piston axis parallel to the axes of the coils. In further embodiments more than three coils may be located at discrete positions spaced around the piston (at locations surrounding the piston), preferably, equally spaced from the piston or otherwise arranged to provide approximately equal forces on the piston.

While various features are described herein in connection with the embodiment of FIGS. 11 and 12 and further features are described herein in connection with FIGS. 3 and 4, it is contemplated that, where possible, features described in connection with one embodiment may be employed in the other embodiment. For example, the outlet configuration with one or more accumulator chambers described above with respect to FIGS. 3 and 4 may be employed in the embodiment of FIGS. 11 and 12.

Alternative Actuator Embodiments

Figure 23A:
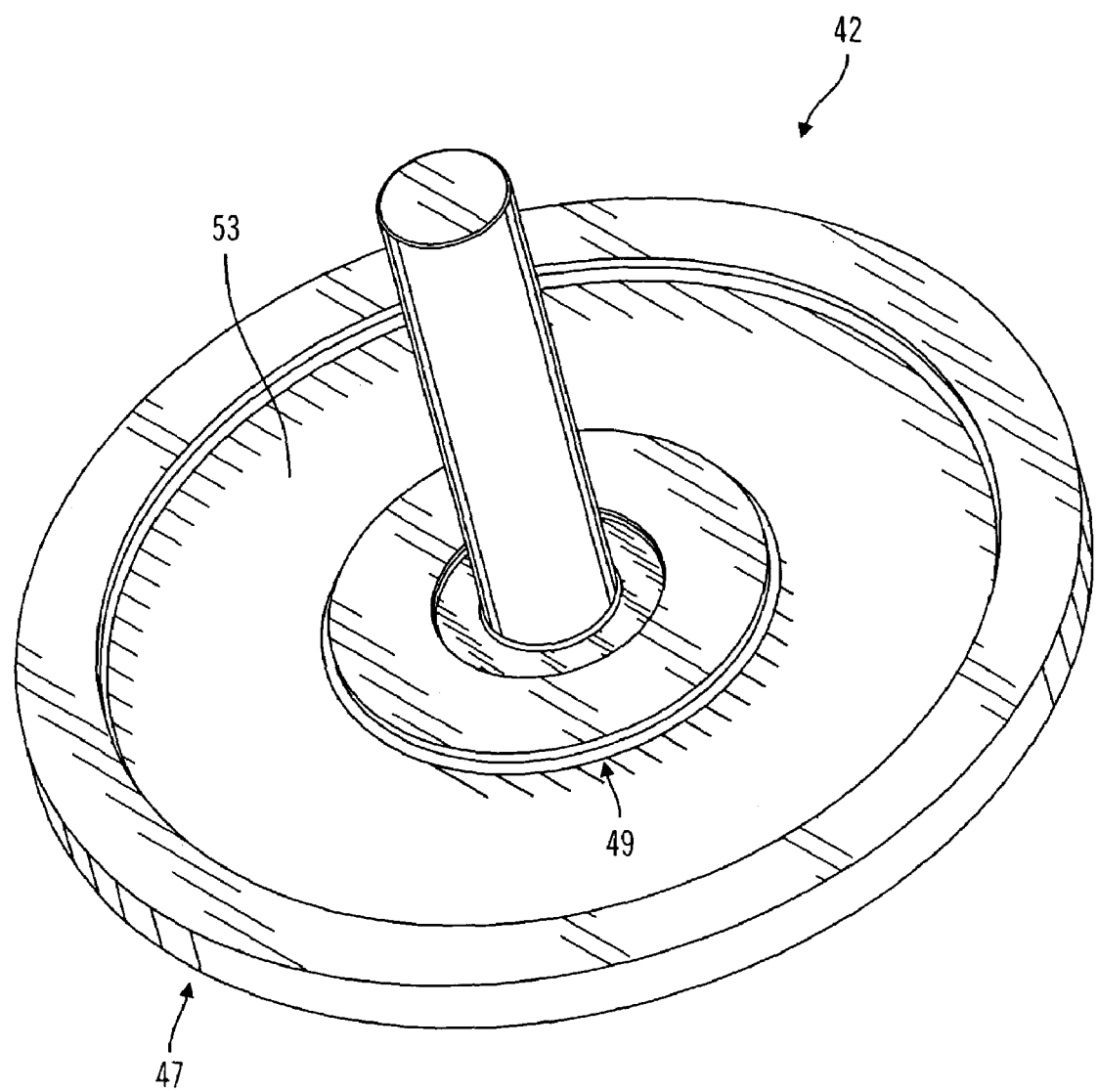
FIG. 23A is a perspective view of an actuator member according to yet a further embodiment of the invention.
Figure 23B:
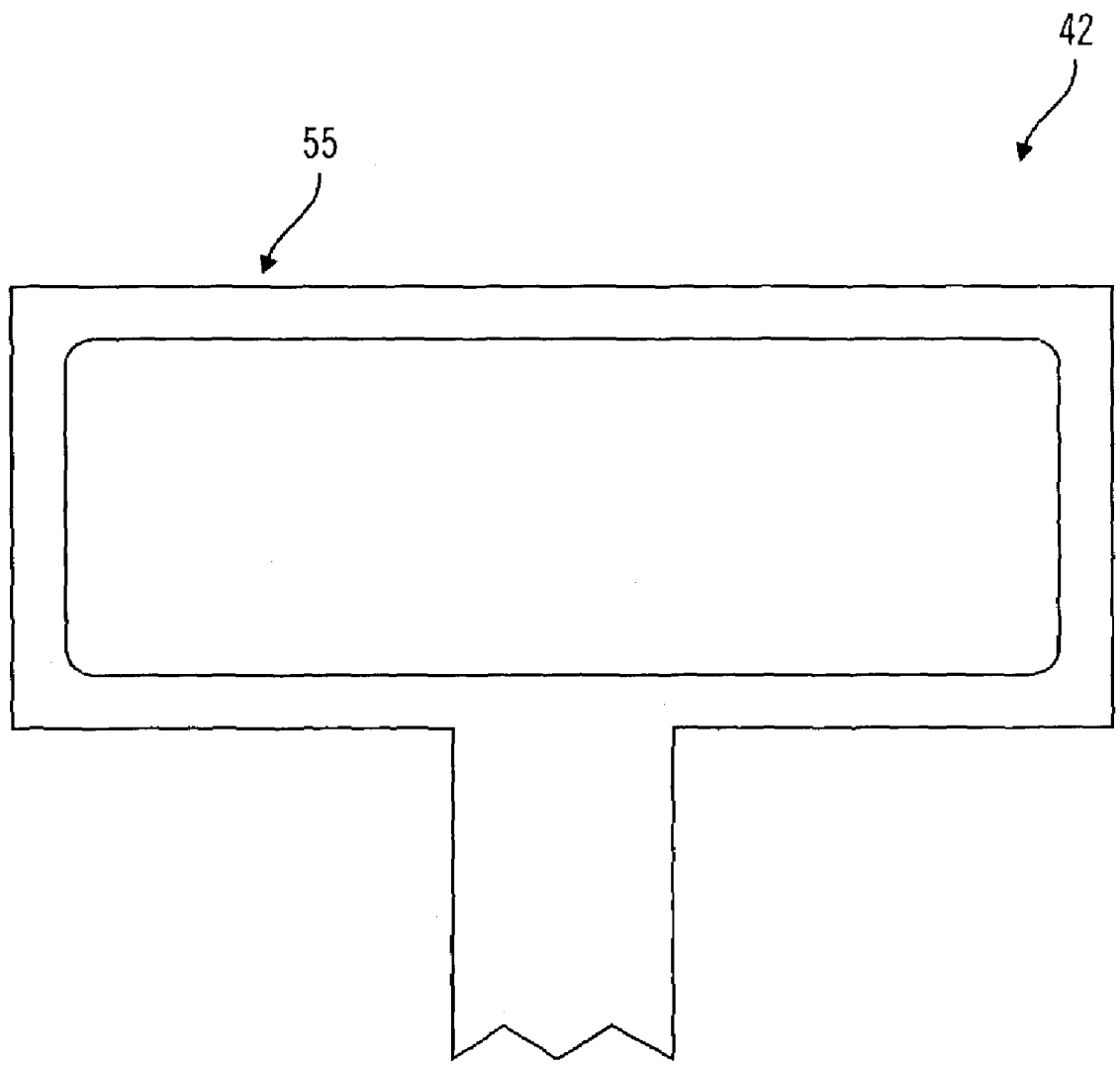
FIG. 23B is a side view of an actuator member covered by a covering material according to yet a further embodiment of the invention.

Another example of an actuator member is shown in FIG. 23A, wherein a s before, the armature portion 42 of the actuator member has a round, disc shape. However, in this embodiment of the actuator member there are no vent holes or other openings extending through the actuator member, nor are there radial struts coupling the annular outer section 47 to the inner section 49 of the armature. Rather, a solid annular midsection 53 couples the annular outer section 47 to the inner section 49. In addition, as shown in FIG. 23B, the surface of the actuator member in this embodiment that comes into contact with medication or other fluids is covered by a covering material 55. The covering material 55 may include, without limitation, materials exhibiting high corrosion resistance such as titanium, which has a history of use in the art with respect to medication or other fluid contact and which should, when welded to the actuator member, face little regulatory resistance. The covering material 55 need not comprise a ferrous material, as long as it covers a ferrous material. In addition to being welded to the actuator member, the covering material 55 may be plated or coated onto the actuator member.

Although the midsection 53 shown in FIG. 23A is solid, in other embodiments it need not be. For example, an embodiment of the midsection 53 may be made with openings extending through it. However, in such an embodiment, the covering material 55, would also be made with corresponding openings, thereby providing a path through which the medication or other fluid may travel.

Figure 24:
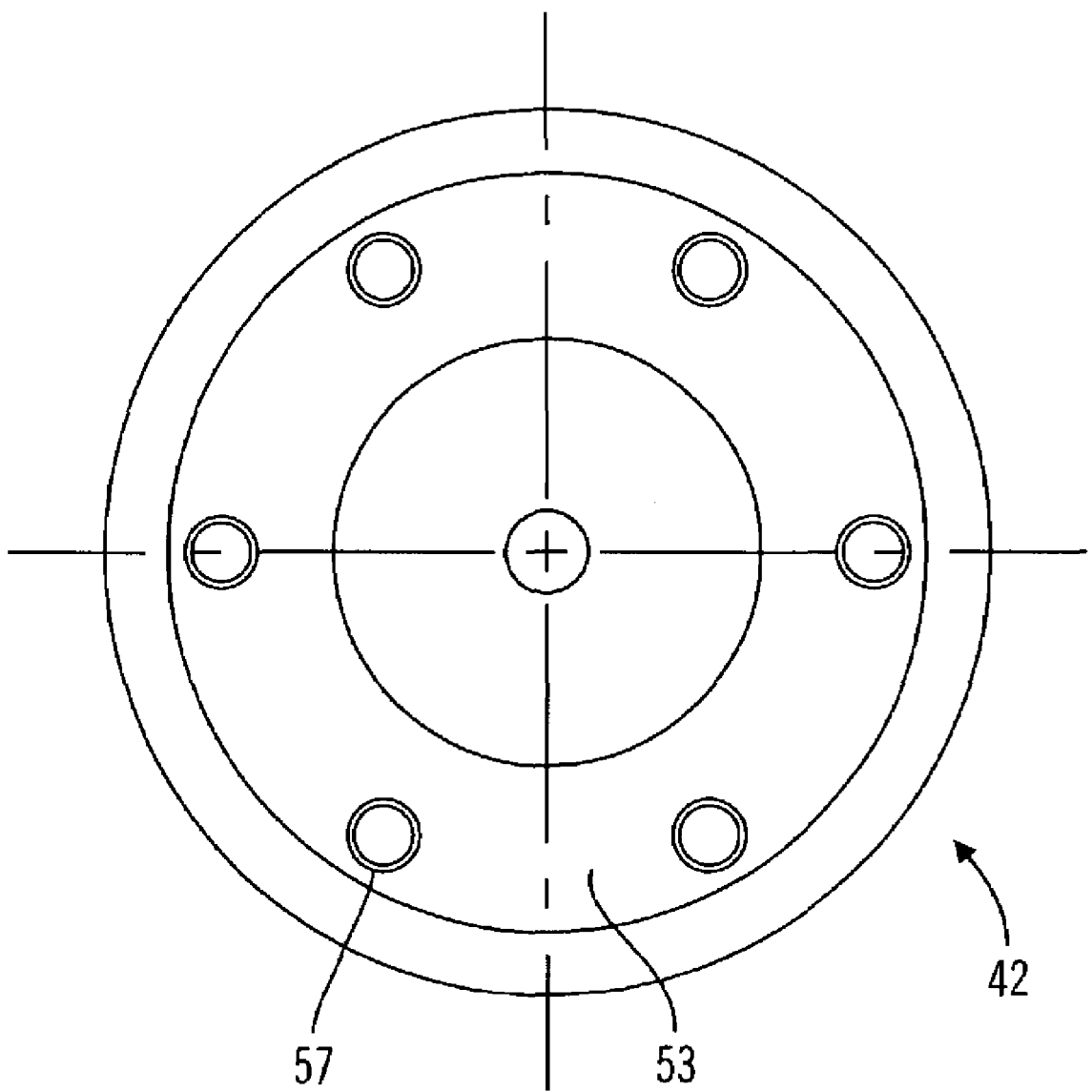
FIG. 24 is a plan view of an actuator member according to yet a further embodiment of the invention.

Yet another example of an actuator member is shown in FIG. 24, wherein, again, the armature portion 42 of the actuator member has a round, disc shape. As can be seen, in this embodiment the midsection 53 is formed with a plurality of through-holes 57. The through-holes 57 may be substantially round and evenly spaced around the midsection 53. This type of through-hole 57 provides less area through which medication or other fluid may pass than the type of openings shown in FIG. 9. In other words, the amount of venting is decreased, which generally results in greater power consumption by the device. However, the embodiment of FIG. 24 is generally less expensive to manufacture than the embodiment shown in FIG. 9. In addition, the embodiment of the actuator member shown in FIG. 25 typically makes less noise than the embodiment of the actuator member shown in FIG. 9. The through-holes 57 need not be round, however; they may be elongated or some other geometry. The through-holes 57 may be laser cut into the midsection 53.

In the embodiment of the actuator member shown in FIG. 24, the diameter and, consequently, the area of the inner section 49 has been increase such that greater damping is achieve while consuming less power. Thus, in FIG. 25, during the first part of the stroke in a pumping operation, medication or other fluid flows radially outward relatively easily. Toward the end of the stroke, the operation of the actuator member is similar to that of a valve closing. Fluid begins to flow through the through-holes 57 and the CV becomes a function of the stroke. Damping occurs right at the end of the stroke, slowing the actuator down, reducing mechanical impact and decreasing power consumption.

The foregoing description of the preferred embodiment of the invention has been presented for the purposes of illustration and description. It is not intended to be exhaustive or to limit the invention to the precise form disclosed. Many modifications and variations are possible in light of the above teaching.

What is claimed is:

1. A drive mechanism for delivery of infusion medium comprising:
   at least one coil winding around a piston channel, the piston channel having an inlet end and an outlet end for communication of infusion medium from the inlet end and out through the outlet end;
   a magnetic return path structure surrounding the piston channel and providing a portion of at least one magnetic return path for said at least one coil;
   a piston located within the piston channel and moveable axially within the piston channel in response to energization of said at least one coil; and
   an armature disposed adjacent said at least one coil, on one side of the piston channel, to provide a further portion of said at least one magnetic return path, the armature having two annular pole faces, wherein both annular pole faces face a same axial direction.

2. The drive mechanism as recited in claim 1, further including an inlet for receiving infusion medium, the inlet in fluid flow communication with the inlet end of the piston channel.

3. The drive mechanism as recited in claim 1, wherein said at least one coil is entirely wound around the piston channel.

4. The drive mechanism of claim 1, wherein
   a clearance between the piston and the piston channel causes a volume of the infusion medium for refilling the piston channel to be greater than a volume of the infusion medium backflowing through the piston channel; and
   the volume of the infusion medium for refilling the piston channel is about 1 to 4 times greater than the volume of the infusion medium backflowing through the piston channel.

5. The drive mechanism of claim 1, wherein a ratio of a diameter of the piston to a diameter of the piston channel is within a range of about 0.990 to about 0.995.

6. The drive mechanism of claim 1, wherein a clearance between the piston and the piston channel averages about 250 microinches.

7. The drive mechanism of claim 1, further comprising:
   an outlet chamber disposed adjacent the coil, on the opposite side of the piston channel relative to the armature for receiving infusion medium from the piston channel.

8. The drive mechanism of claim 1, further comprising:
a valve member being moveable in response to axial movement of the piston within the piston channel,
wherein a clearance between the piston and the piston channel is sufficient to restrict the infusion medium within the piston channel such that pressure on the infusion medium caused by movement of the piston opens the valve member.

9. The drive mechanism of claim 1, further comprising:
an outlet in flow communication with the outlet end of the piston channel, for discharging infusion medium from the piston channel.

10. The drive mechanism of claim 1, wherein the two annular pole faces are concentric.

11. The drive mechanism of claim 10, wherein the two annular pole faces comprise an inner pole face and an outer pole face, wherein the inner pole face has a width greater than a width of the outer pole face.

12. A drive mechanism for delivery of infusion medium comprising:
at least one coil surrounding a piston channel, the piston channel having an inlet end and an outlet end for communication of infusion medium from the inlet end and out through the outlet end;
a magnetic return path structure surrounding the piston channel and providing a portion of at least one magnetic return path for said at least one coil;
a piston located within the piston channel and moveable axially within the piston channel in response to energization of said at least one coil; and
an armature disposed adjacent said at least one coil, on one side of the piston channel, to provide a further portion of said at least one magnetic return path, the armature having two pole faces, wherein each pole face is directed substantially axially with respect to the piston channel,
wherein said at least one coil includes a coil having windings which surround the piston channel, and
wherein said magnetic return path structure includes a coil cup composed of a magnetizable material, the coil cup having:
a generally annular inner wall;
a generally annular outer wall;
a generally annular interior between the inner and outer walls, the annular interior containing the coil; and
a central channel surrounded by the inner wall, the central channel of the coil cup being substantially coaxial with the coil;
wherein the inner wall has one end defining an inner pole surface and the outer wall has a second end defining an outer pole surface, the inner and outer pole surfaces acting with the two pole faces of the armature to provide an electromagnetic flux path upon electrical activation of the coil.

13. The drive mechanism as recited in claim 12, wherein the coil is capable of being electrically activated to provide an electromagnetic field;
wherein the armature is moveable toward the coil, in response to the electromagnetic field produced by an activation of the coil; and
wherein the armature includes radial struts for conducting electromagnetic flux in a radial direction.

14. The drive mechanism as recited in claim 13, wherein the radial struts are made of a magnetizable material.

15. The drive mechanism as recited in claim 14, wherein the two pole faces of the armature comprise an annular inner pole surface and an annular outer pole surface, each made of a magnetizable material, wherein the inner pole surface of the armature faces the inner pole surface of the inner coil cup wall, and outer pole surface of the armature faces the outer pole surface of the outer coil cup wall.

16. The drive mechanism as recited in claim 15, wherein the radial struts couple the inner and outer pole surfaces of the armature.

17. The drive mechanism as recited in claim 15, wherein the armature further has apertures between the radial struts.

18. The drive mechanism as recited in claim 15, wherein at least one of the inner and outer pole surfaces of the armature are textured.

19. A drive mechanism for delivery of infusion medium comprising:
at least one coil having windings surrounding a piston channel, the piston channel having an inlet end and an outlet end for communication of infusion medium from the inlet end and out through the outlet end, wherein the at least one coil is capable of being electrically activated to provide an electromagnetic field;
a magnetic return path structure surrounding the piston channel and providing a portion of at least one magnetic return path for said at least one coil;
a piston located within the piston channel and moveable axially within the piston channel in response to energization of said at least one coil; and
an armature disposed adjacent said at least one coil, on one side of the piston channel, to provide a further portion of said at least one magnetic return path, the armature having two pole faces within at least one magnetic return path, wherein each pole face is directed substantially axially with respect to the piston channel;
wherein said magnetic return path structure includes a coil cup composed of a magnetizable material, the coil cup having:
a generally annular inner wall;
a generally annular outer wall;
a generally annular interior between the inner and outer walls, the annular interior containing the coil; and
a central channel surrounded by the inner wall, the central channel of the coil cup being substantially coaxial with the coil;
wherein the inner wall has one end defining an inner pole surface and the outer wall has a second end defining an outer pole surface, the inner and outer pole surfaces acting with the two pole faces of the armature to provide an electromagnetic flux path upon electrical activation of the coil;
wherein the armature is moveable toward the coil, in response to the electromagnetic field produced by an activation of the coil;
wherein the armature includes radial struts for conducting electromagnetic flux in a radial direction;
wherein the two pole faces of the armature comprise an annular inner pole surface and an annular outer pole surface, each made of a magnetizable material, wherein the inner pole surface of the armature faces the inner pole surface of the inner coil cup wall, and outer pole surface of the armature faces the outer pole surface of the outer coil cup wall; and
wherein the inner pole surface of the armature is spaced from the inner wall of the coil cup by a first gap and the outer pole surface of the armature is spaced from the outer wall of the coil cup by a second gap when the coil is not electrically activated, and wherein the second gap is larger than the first gap.

20. A method for making an infusion medium delivery device, the method comprising:
providing at least one coil winding around a piston channel, the piston channel having an inlet end and an outlet end for communication of infusion medium from the inlet end and out through the outlet end;
providing a piston through the piston channel and moveable axially within the piston channel in response to energization of said at least one coil;
providing a magnetic return path structure surrounding the piston channel and providing a portion of at least one magnetic return path for said at least one coil; and
providing an armature disposed adjacent said at least one coil, on one side of the piston channel, to provide a further portion of said at least one magnetic return path, the armature having two annular pole faces, wherein both annular pole faces face a same axial direction.

21. The method as recited in claim 20, further including providing an inlet for receiving infusion medium, the inlet in fluid flow communication with the inlet end of the piston channel.

22. The method as recited in claim 20, wherein said at least one coil is entirely wound around the piston channel.

23. The drive mechanism of claim 20, further comprising:
providing an outlet in flow communication with the outlet end of the piston channel, for discharging infusion medium from the piston channel.

24. The method of claim 20, wherein the two annular pole faces are concentric.

25. The method of claim 24, wherein the two annular pole faces comprise an inner pole face and an outer pole face, wherein the inner pole face has a width greater than a width of the outer pole face.

26. The method as recited in claim 20, further including:
providing an outlet chamber in flow communication with the outlet end of the piston channel, the outlet chamber disposed adjacent the at least one coil, on the opposite side of the piston channel relative to the armature, for receiving infusion medium from the channel;
providing a valve member moveable between open and closed positions to selectively allow and inhibit fluid flow from the piston channel, the valve member being moveable in response to axial movement of the piston within the piston channel; and
providing an outlet port in flow communication with the outlet chamber.

27. The method as recited in claim 26, wherein the valve member is located within the outlet chamber.

28. A method for making an infusion medium delivery device, the method comprising:
providing at least one coil surrounding a piston channel, the piston channel having an inlet end and an outlet end for communication of infusion medium from the inlet end and out through the outlet end;
providing a piston through the piston channel and moveable axially within the piston channel in response to energization of said at least one coil;
providing a magnetic return path structure surrounding the piston channel and providing a portion of at least one magnetic return path for said at least one coil; and
providing an armature disposed adjacent said at least one coil, on one side of the piston channel, to provide a further portion of said at least one magnetic return path, the armature having two pole faces, wherein each pole face is directed substantially axially with respect to the piston channel,
wherein providing said magnetic return path structure includes providing a coil cup composed of a magnetizable material and having:
a generally annular inner wall;
a generally annular outer wall;
a generally annular interior between the inner and outer walls, the annular interior containing the coil; and
a central channel surrounded by the inner wall, the central channel of the coil cup being substantially coaxial with the coil;
wherein the inner wall has one end defining an inner pole surface and the outer wall has a second end defining an outer pole surface, the inner and outer pole surfaces acting with the two pole faces of the armature to provide an electromagnetic flux path upon electrical activation of the coil.

29. The method as recited in claim 28, wherein providing an armature having two pole faces includes providing an armature having an annular inner pole surface and an annular outer pole surface, each made of a magnetizable material, wherein the inner pole surface of the armature faces the inner pole surface of the inner wall of the coil cup, and outer pole surface of the armature faces the outer pole surface of the outer wall of the coil cup.

30. The method as recited in claim 29, wherein the armature includes radial struts for conducting electromagnetic flux in a radial direction.

31. A method for delivery of infusion medium comprising:
providing at least one coil winding around a piston channel, the piston channel having an inlet end and an outlet end for communication of infusion medium from the inlet end and out through the outlet end;
providing a piston through the piston channel and moveable axially within the piston channel in response to energization of said at least one coil;
providing a magnetic return path structure surrounding the piston channel and providing a portion of at least one magnetic return path for said at least one coil;
providing an armature disposed adjacent said at least one coil, on one side of the piston channel, to provide a further portion of said at least one magnetic return path, the armature having two annular pole faces, wherein both annular pole faces face a same axial direction;
providing an outlet chamber in flow communication with the outlet end of the piston channel, the outlet chamber disposed adjacent the at least one coil, on the opposite side of the piston channel relative to the armature, for receiving infusion medium from the piston channel;
providing a valve member moveable between open and closed positions to selectively allow and inhibit fluid flow from the piston channel, the valve member being moveable in response to axial movement of the piston within the piston channel;
providing an outlet port in flow communication with the outlet chamber;
receiving infusion medium through the inlet;
urging the piston and armature toward a retracted position to form a piston chamber between one end of the piston and the valve member;
filling the piston chamber with the infusion medium by passing a volume of the infusion medium received on an armature side of the coil from the inlet through the piston channel to the piston; and
electrically activating the coil to provide an electromagnetic field to move the armature and piston toward a forward position to deliver a volume of infusion medium through the outlet port.

32. The method as recited in claim 31, further including: moving the piston toward the forward position under the force of the electromagnetic field to compress a volume of the piston chamber and force the valve member to an open position;

discharging the infusion medium from the piston chamber, through the open valve member and into the outlet chamber, upon the piston being moved to the forward position; and delivering the infusion medium discharged from the outlet chamber through the outlet port.

33. A drive mechanism for delivery of infusion medium comprising:

an inlet for receiving infusion medium;

a piston channel for communication of infusion medium received by the inlet;

a coil winding around the piston channel;

a magnetic return path structure surrounding the piston channel and providing a portion of at least one magnetic return path for the coil;

a piston located within the piston channel and moveable axially within the piston channel to drive infusion medium into the piston channel;

an armature disposed adjacent the coil, on one side of the piston channel;

an outlet chamber disposed adjacent the coil, on the opposite side of the piston channel relative to the armature for receiving infusion medium from the channel; and an outlet in flow communication with the outlet chamber, for discharging infusion medium from the outlet chamber, wherein the coil is capable of being electrically activated to provide an electromagnetic field;

wherein the armature is moveable toward the coil, in response to the electromagnetic field produced by an activation of the coil; and wherein the armature comprises a pair of annular pole surfaces, both annular pole surfaces facing a same axial direction.

34. The drive mechanism of claim 33, wherein the armature further comprises radial struts for conducting electromagnetic flux between the pair of annular pole surfaces in a radial direction.

35. The drive mechanism of claim 33, wherein the pair of annular pole surfaces are concentric.

36. The drive mechanism of claim 35, wherein the pair of annular pole surfaces comprise an inner pole surface and an outer pole surface, wherein the inner pole surface has a width greater than a width of the outer pole surface.

* * * * *